(12) United States Patent
Kumar

(10) Patent No.: US 6,561,805 B2
(45) Date of Patent: *May 13, 2003

(54) UNIVERSAL IMPLANT DELIVERY SYSTEM

(75) Inventor: Ajay Kumar, Palmdale, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/760,602

(22) Filed: Jan. 16, 2001

(65) Prior Publication Data

US 2001/0019816 A1 Sep. 6, 2001

Related U.S. Application Data

(63) Continuation-in-part of application No. 09/374,087, filed on Aug. 12, 1999, now Pat. No. 6,312,260.
(60) Provisional application No. 60/176,442, filed on Jan. 14, 2000, provisional application No. 60/227,110, filed on Aug. 22, 2000, and provisional application No. 60/228,644, filed on Aug. 29, 2000.

(51) Int. Cl.$^7$ ................................................ A61C 8/00
(52) U.S. Cl. ...................................... 433/174; 206/368
(58) Field of Search ................................ 433/173, 174, 433/201.1, 176; 206/431, 368, 63.5

(56) References Cited

U.S. PATENT DOCUMENTS

| | | |
|---|---|---|
| 2,347,567 A | 4/1944 | Kresse |
| 3,346,135 A | 10/1967 | Haitsch |

(List continued on next page.)

FOREIGN PATENT DOCUMENTS

| | | |
|---|---|---|
| CA | 2232009 | 3/1998 |
| DE | 9014729.4 | 1/1991 |
| EP | 05 293122 | 9/1993 |
| EP | 0 630 621 A1 | 12/1994 |
| WO | WO 96/25895 | 6/1996 |
| WO | WO 97/20518 | 6/1997 |
| WO | WO 98/52490 | 11/1998 |
| WO | WO 98/53755 | 12/1998 |

OTHER PUBLICATIONS

Copy of International Search Report corresponding to PCT/US99/15780.
Copy of International Search Report corresponding to PCT/US99/15944.
Copy of International Seacr Report corresponding to PCT/US99/18339.

Primary Examiner—Todd E. Manahan
(74) Attorney, Agent, or Firm—Knobbe, Martens, Olson & Bear, LLP.

(57) ABSTRACT

A dental implant delivery system and assembly for inserting a dental implant into a pre-drilled bore in the jawbone is discussed. The dental implant assembly system includes an implant body to which is attached a healing cap for covering the central socket in the implant body during the healing period. The healing cap is mechanically coupled to the implant body before the insertion procedure by a coupling screw extending through bore in the healing cap into the central socket of the implant body. A recess in the bottom of the healing cap mates with a protrusion on the top of the implant body such that the healing cap is prevented from rotating relative to the implant body. A torque drive adapter engages the top of the healing cap for easy manipulation of the implant body/healing cap during the insertion procedure. The dental implant, healing cap, coupling screw and torque drive adapter are packaged together in a sterile package. Removing the top portion of the sterile package exposes the top of the torque drive adapter. A tool is attached to the adapter and used to transfer the implant to the jawbone and to insert the implant into the pre-drilled bore. The torque drive adapter is disengaged from the healing cap after the insertion procedure thereby leaving the implant body and healing cap in the jawbone.

25 Claims, 19 Drawing Sheets

U.S. PATENT DOCUMENTS

| | | |
|---|---|---|
| 3,481,712 A | 12/1969 | Bersnstein et al. |
| 4,158,256 A | 6/1979 | Wiland et al. |
| 4,187,609 A | 2/1980 | Edelman |
| 4,465,463 A | 8/1984 | Olde |
| 4,553,942 A | 11/1985 | Sutter |
| 4,600,388 A | 7/1986 | Linkow |
| 4,722,688 A | 2/1988 | Lonca |
| 4,856,648 A | 8/1989 | Krueger |
| 4,856,994 A | 8/1989 | Lazzara et al. |
| 4,955,811 A | 9/1990 | Lazzara et al. |
| 5,013,242 A | 5/1991 | Prezmecky |
| 5,030,096 A | 7/1991 | Hurson et al. |
| 5,062,800 A | 11/1991 | Niznick |
| 5,100,323 A | 3/1992 | Friedman et al. |
| 5,105,690 A | 4/1992 | Lazzara et al. |
| 5,108,288 A | 4/1992 | Perry |
| 5,158,458 A | 10/1992 | Perry |
| 5,213,500 A | 5/1993 | Salazar et al. |
| 5,254,005 A | 10/1993 | Zuest |
| 5,290,171 A | 3/1994 | Daftary et al. |
| 5,297,561 A | 3/1994 | Hulon |
| 5,302,125 A | 4/1994 | Kownacki et al. |
| 5,306,309 A | 4/1994 | Wagnet et al. |
| 5,312,254 A | 5/1994 | Rosenlicht |
| 5,322,443 A | 6/1994 | Beaty |
| 5,336,090 A | 8/1994 | Wilson, Jr. et al. |
| 5,338,196 A | 8/1994 | Beaty et al. |
| 5,368,160 A | 11/1994 | Leuschen et al. |
| 5,368,483 A | 11/1994 | Sutter et al. |
| 5,417,570 A | 5/1995 | Zuest et al. |
| 5,433,330 A | 7/1995 | Yatsko et al. |
| 5,437,550 A | 8/1995 | Beaty et al. |
| 5,453,010 A | 9/1995 | Klein |
| 5,462,436 A | 10/1995 | Beaty |
| 5,507,463 A | 4/1996 | Klein |
| 5,525,314 A | 6/1996 | Hurson |
| 5,538,428 A | 7/1996 | Staubli |
| 5,558,230 A | 9/1996 | Fischer et al. |
| 5,564,924 A | 10/1996 | Kwan |
| 5,569,037 A | 10/1996 | Moy et al. |
| 5,582,299 A | 12/1996 | Lazzara et al. |
| 5,622,500 A | 4/1997 | Niznizk |
| 5,636,991 A | 6/1997 | Mays |
| 5,651,675 A | 7/1997 | Singer |
| 5,683,464 A | 11/1997 | Wagner et al. |
| 5,692,904 A | 12/1997 | Beaty et al. |
| 5,733,124 A | 3/1998 | Kwan |
| 5,755,575 A | 5/1998 | Biggs |
| 5,887,707 A | 3/1999 | Anascavage et al. |
| 5,904,483 A | 5/1999 | Wade |
| 5,961,330 A | 10/1999 | Harison |
| 5,964,591 A | 10/1999 | Beaty et al. |
| 5,967,305 A | 10/1999 | Blonder et al. |
| 5,979,643 A | 11/1999 | Blonder et al. |
| 5,996,779 A * | 12/1999 | Klardie et al. ............ 206/63.5 |
| 6,247,932 B1 * | 6/2001 | Sutter ........................ 433/173 |
| 6,247,933 B1 | 6/2001 | Wagner et al. |

* cited by examiner

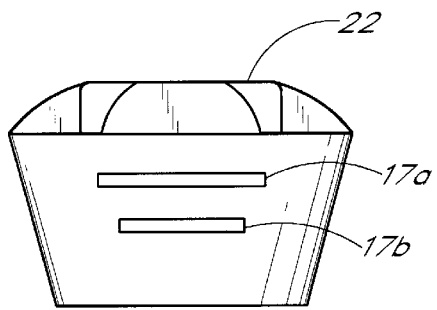
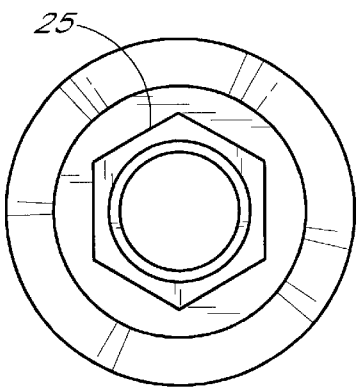
FIG. 4A               FIG. 4B
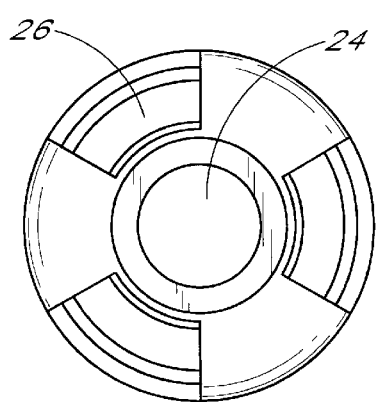
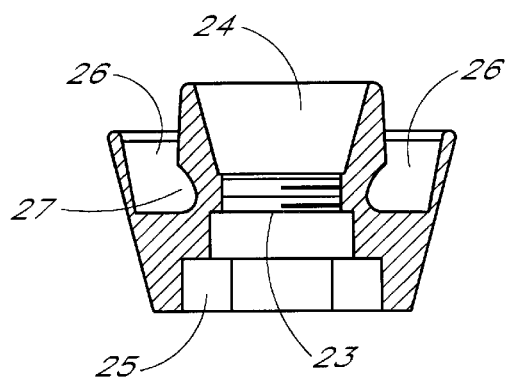
FIG. 4C               FIG. 4D

UNIVERSAL IMPLANT DELIVERY SYSTEM

PRIORITY INFORMATION

This application is a continuation-in-part of U.S. patent application Ser. No. 09/374,087, filed Aug. 12, 1999 now U.S. Pat. No. 6,312,260 and this application claims priority and benefit under 35 U.S.C. §119(e) of U.S. Provisional Application Ser. No. 60/176,442, filed Jan. 14, 2000, U.S. Provisional Application Ser. No. 60/227,110, filed Aug. 22, 2000, and U.S. Provisional Application Ser. No. 60/228,644, filed Aug. 29, 2000.

BACKGROUND OF THE INVENTION

1. Field of the Invention

The present invention relates generally to dental implants and, more particularly, to a dental implant delivery system that includes a threaded implant body with a pre-attached healing cap, which are packaged in a sterile vial, and can be quickly and safely placed into the jaw as a single unit.

2. Related Art

Dental implants are placed in the jaw to provide support for a dental restoration, fixed bridge or removable partial denture. Dental implants provide good chewing function and also improve the patient's cosmetic appearance thereby allowing the patient to smile, speak, and interact with others with greater confidence.

One type of dental implant widely used in the industry is typically referred to as a "threaded" implant. Threaded implants have an externally threaded body portion which is screwed into a pre-drilled hole (i.e. an osteotomy) in the patient's upper or lower jawbone. Typically, the threaded implant body is formed with a central threaded socket accessible through the overlying gum tissue for receiving and supporting one or more dental attachments or components. Types of attachments and components that are received by the central socket include healing caps, impression copings and abutments. In turn, some of these attachments and components are useful to fabricate and/or support the prosthodontic restoration.

Dental implants are typically packaged as an assembly including all the tools necessary for the insertion of the implant into an osteotomy formed in the jaw. A typical threaded implant assembly includes a threaded implant body, an implant carrier, an insertion post, a coupling screw and a healing cap. Conventionally, these components are sterilized, pre-assembled and packaged in a sterile vial. The implant carrier, insertion post, and coupling screw are tools which are used during the insertion of the implant body. Typically, the implant carrier, insertion post, coupling screw and vial are discarded after the implant body has been inserted into the osteotomy. The healing cap seals and protects the central socket of the implant body during the initial healing period, and then is discarded.

During the insertion of a conventional threaded implant, the insertion post is mechanically coupled to the top of the implant body by a coupling screw which traverses a central through-cavity in the insertion post and is threaded into the central threaded socket in the implant body. Typically, the bottom end of the insertion post is formed with a hexagonal cavity that irrotationally mates with a corresponding hexagonal protrusion formed on the top of the implant body thereby preventing any relative rotation between the insertion post and implant body while coupled.

An implant carrier is releasably coupled to the top of the insertion post and provides the dental practitioner with a means to grip and manipulate the assembly during the initial implantation procedure. Typically, the implant carrier is formed with a generally hexagonal internal passage at its bottom end which mates with a generally hexagonal outer surface near the top of the insertion post. The dental practitioner uses the implant carrier to manipulate the implant body into the proper location within the jawbone. Torque is applied to the implant carrier which is transferred, via the insertion post, to the threaded implant body.

In use, the first step of a typical implantation procedure involves making an incision in the patient's gum tissue. A portion of the gum tissue is then folded back and an osteotomy is drilled in the jawbone. The diameter of the osteotomy is equal to or slightly smaller than the diameter of the implant body. The implant carrier is then used to transport the threaded implant assembly to the surgical site. The implant carrier is gripped by the practitioner and is used to manipulate the implant body into the correct position and then to partially screw the threaded implant body into the osteotomy.

Once the implant body has been initially placed in the osteotomy and tightened manually, the implant carrier is decoupled from the insertion post and is removed from the surgical site. If necessary, a suitable wrench or dental hand piece is then used to engage the insertion post and drive the implant to its final depth within the osteotomy. The coupling screw is then removed and the insertion post is decoupled from the implant body leaving only the implant body in the patient's mouth.

The healing cap is housed in a cavity formed in the top of the implant carrier where it is contained by a paper barrier until needed. At this point, the healing cap is removed from the implant carrier and is threaded into the central socket of the implant body. Typically, a tool with a hexagonal tip is inserted into a corresponding mating hexagonal recess located in the top center of the healing cap and is used to apply torque to tighten the healing cap. The healing cap protects the implant socket against bone or tissue ingrowth during the initial healing period, and also prevents the entry of bacteria or other contaminants into the central socket of the implant body.

The insertion of the implant body and healing cap is then followed by an initial healing period in which the bone is allowed to surround and retain the implant (i.e. "osseointegrate" with the implant) and the gum tissue is allowed to heal over the implant body and healing cap. For implants placed in the mandible, healing typically requires about three months; for implants in the maxilla, the healing period typically requires about six months.

After the implant body has sufficiently osseointegrated with the jawbone, the gum tissue is re-opened by making an incision and the gum tissue is folded back to expose the healing cap. A hexagonal tool is inserted into the recess in the top of the healing cap and torque is applied to rotate the healing cap out of the implant socket and to remove it from the implant body. During this step of the procedure, great care must be used to remove the healing cap without disturbing the position of the implant body. Any disturbance of the implant body during the removal of the healing cap could damage the osseointegration between the implant body and the jawbone. Damage to the osseointegration is very undesirable and could endanger the entire restoration process by destabilizing the implant. In addition, any movement of the implant body could result in gaps or spaces between the implant body and jawbone which could in turn lead to infection by bacteria and/or other contaminants.

After the healing cap has been unscrewed and removed from the patient's mouth, a suitable healing abutment is inserted into the central socket. The healing abutment extends through the gum tissue overlying the implant site. A second healing period then ensues in which the gum tissue is allowed to heal around the post-osseointegration healing abutment. Typically, this second healing period lasts from four to eight weeks.

After the second healing period has ended, the healing abutment is removed from the implant body. Typically, an impression is taken of the patient's mouth to fabricate a prosthesis or dental restoration. An abutment supporting the final restoration is then attached to the implant body. Lastly, the restoration is cemented or screwed to the abutment and/or implant body to complete the placement of the prosthodontic restoration in the patient's mouth.

The procedure described above for installing a threaded dental implant is commonly used by dental practitioners. However, this procedure suffers from several significant shortcomings. For example, the dental practitioner may choose to attach a wrench or dental hand piece to the threaded implant assembly before transporting the assembly to the surgical site. The dental practitioner may choose to modify the procedure in this manner because it can be difficult to attach the wrench or dental hand piece to the implant assembly inside the patient's mouth. This modification requires the dental practitioner to remove the implant carrier from the implant assembly by griping the implant assembly with one hand and pulling the implant carrier away from the implant assembly with the other hand. Typically, the wrench or dental hand piece is then attached to the implant assembly by griping the implant assembly with one hand while pushing the wrench or hand piece towards the dental assembly with the other hand. This procedure is undesirable for several reasons. For example, touching the implant assembly can damage and/or contaminate the assembly. This procedure also requires the additional step of removing the implant carrier from the implant assembly.

Thus, there exists a need for an improved means for placing a threaded dental implant and healing cap into an osteotomy in a more efficient and safe manner than has heretofore been available with conventional methods.

SUMMARY OF THE INVENTION

Accordingly, an aspect of the present invention includes a method for inserting a dental implant comprising drilling a hole in the jawbone below the gums, removing a top portion of a package, securing a tool to the implant while the dental implant is supported by a remaining portion of the package, removing the dental implant from the remaining portion of the package, transporting the dental implant to the hole in the jawbone, applying torque to the dental implant via the tool, and disengaging the tool from the dental implant.

Another aspect of the present invention is a package for storing a dental implant assembly in a sterile environment. The package comprises a first portion and a second portion that is attached to the first portion. The dental implant assembly includes at least a dental implant and an adapter that is secured to the dental implant. The package is configured such that when the first portion is separated from the second portion an upper portion of the adapter is exposed while the dental implant remains contained within the second portion.

Yet another aspect of the present invention is a dental implant delivery system to be used in implanting a dental implant within an osteotomy formed in a jawbone. The system comprises a dental implant having a top end and a bottom end. The bottom end is insertable into the osteotomy. The dental implant also includes a threaded central socket extending from the top end toward the bottom end. The socket is open at the top end of the dental implant. The system also includes a healing cap having a top and a bottom and a central bore extending therethrough. The healing cap is sized and shaped so as to sealingly engage the top end of the dental implant to substantially prevent bacteria or debris from entering the central socket during an initial healing period. The healing cap further comprises a first connector for receiving a torque drive adapter. The torque drive adapter has a top end and a bottom end. The bottom end of the adapter is formed with a second connector which is engageable with the first connector in the top of the cap for engaging and applying torque to the cap to thread the dental implant into the hole formed in the jaw bone. The top end of the dental implant and/or the bottom of the healing cap further having a rotational lock to prevent relative rotation of the healing cap and the dental implant when the healing cap is engaged with the dental implant. A coupling screw has a head seated against the top of the healing cap and a shaft extending through the central bore in the healing cap and threading into the threaded socket in the dental implant. The coupling screw securely couples the healing cap to the implant body. The system also includes a package that includes a top piece and a bottom piece. The dental implant, the healing cap, the coupling screw, and the torque driver adapter are pre-assembled and packaged and supported in the package such that when the top piece is removed the top end of the torque driver adapter is exposed.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed herein.

BRIEF DESCRIPTION OF THE DRAWINGS

These and other features, aspects and advantages of the present invention will now be described with reference to the drawings of a preferred embodiment, which embodiment is intended to illustrate and not to limit the invention, and in which figures:

FIG. 4A is a side view of the healing cap shown in FIG. 2;

FIG. 4B is a bottom view of the healing cap shown in FIG. 4;

FIG. 4C is a top view of the healing cap shown in FIG. 4;

FIG. 4D is a cross-sectional view of the healing cap shown in FIG. 4;

DETAILED DESCRIPTION OF THE PREFERRED EMBODIMENTS

Figure 1A:
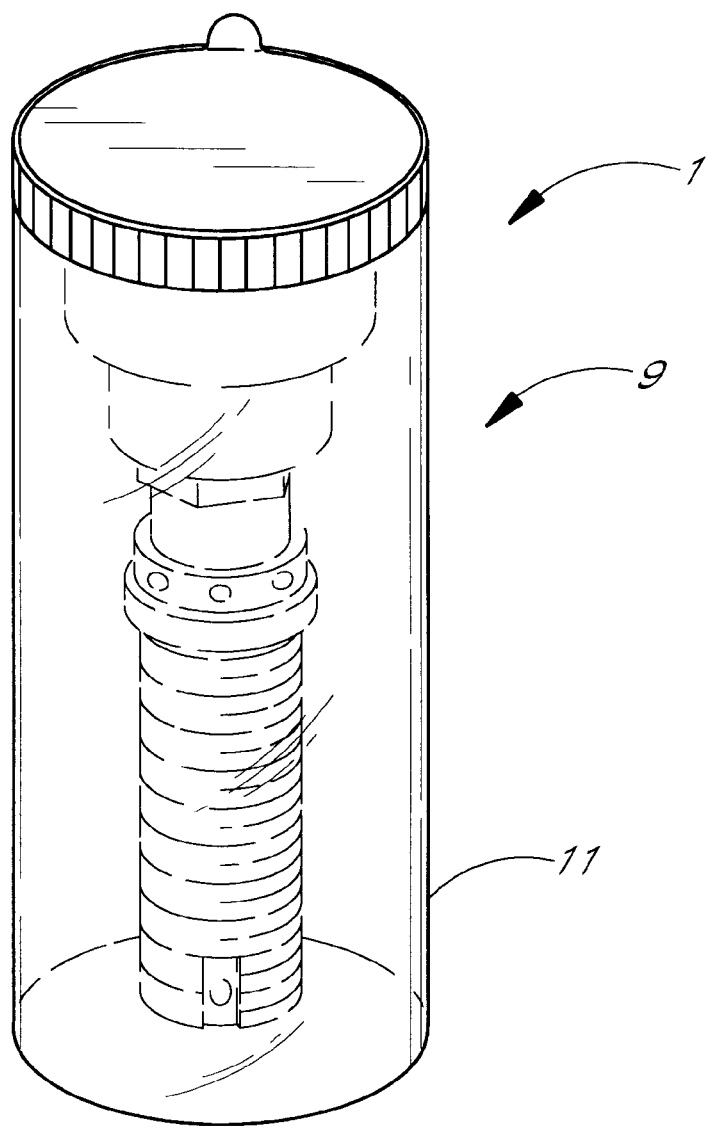
FIG. 1A is a perspective view of a conventional threaded dental implant assembly packaged in a sterile vial in accordance with the prior art.
Figure 1B:
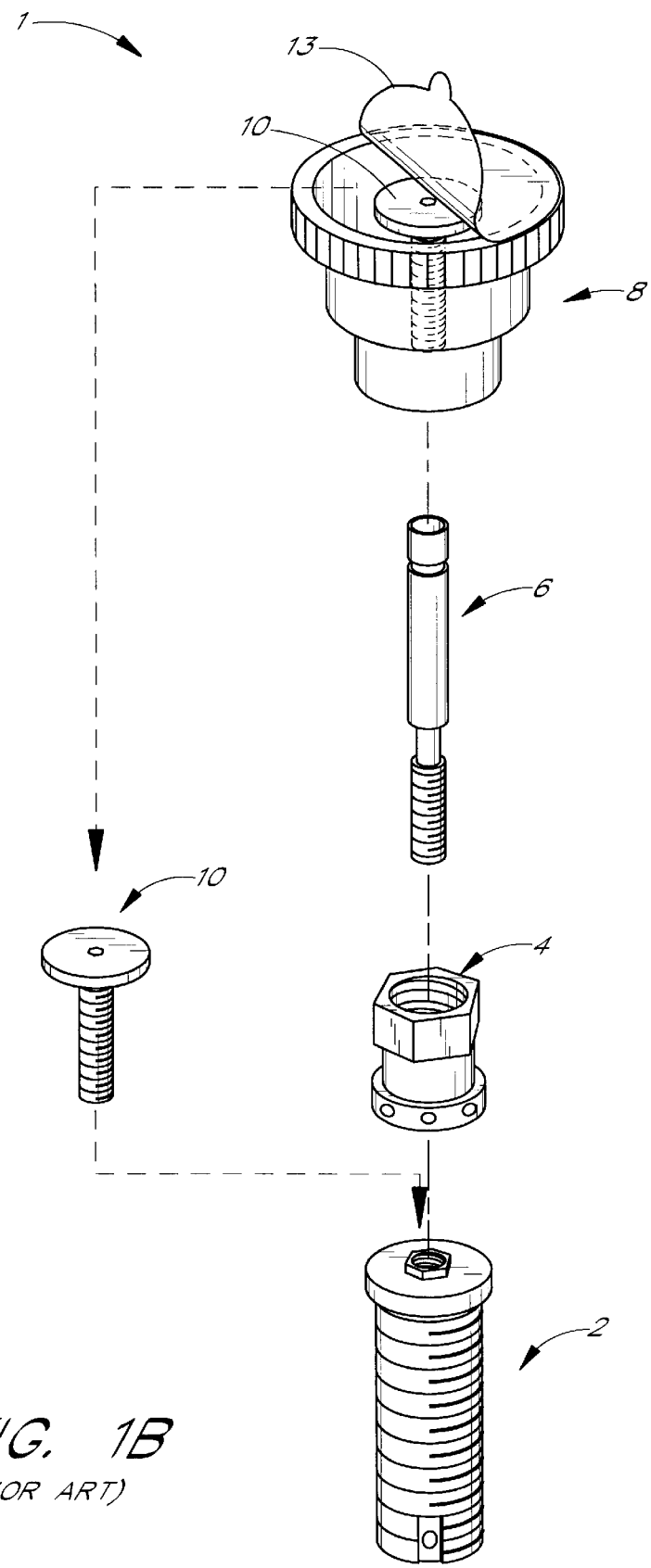
FIG. 1B is an exploded view of the conventional threaded dental implant assembly.

The insertion of a conventional threaded implant body into an osteotomy formed in a jawbone is a difficult and time consuming procedure. As shown in FIGS. 1A and 1B, a conventional implant assembly 1 and delivery system typically includes an implant body 2, an insertion post 4 coupled to the implant body 2 by a coupling screw 6, an implant carrier 8 coupled to the insertion post 4, and a healing cap 10. Conventionally, these components are sterilized, pre-assembled and packaged within a sterile vial 9 (see FIG. 1A). The illustrated vial 9 comprises a lower portion 11, which is removably attached to the implant carrier 8.

In use, the dental practitioner drills a hole (i.e. an osteotomy) in the patient's jawbone. The dental practitioner then grips the implant carrier 8 and removes the implant assembly from the vial 9. He or she then transports the implant assembly 1 to the surgical site, and manipulates the implant body 2 into position over the osteotomy. Once the implant body 2 is properly positioned, the dental practitioner applies torque to the implant carrier 8 to begin screwing the implant body into the osteotomy. If necessary, the implant carrier 8 is then decoupled from the insertion post 4 and a tool, such as a dental handpiece or driver, is attached to the insertion post to drive the implant body the rest of the way into the osteotomy. After the implant body is properly seated, the insertion post is decoupled from the implant body by removing the coupling screw. To protect against infection, a healing cap 10 is screwed into the central socket of the implant body 2 to cover the socket during the initial healing period. The healing cap 10 is typically packaged within a hollow portion of the carrier 8 and is covered by a sterile foil 13, which can be peeled back to access the healing cap 10.

The process described above can has several drawbacks. For example, the process can be very difficult and requires much skill and attention to detail. If the healing cap 10 is tightened too much, the healing cap 10 may be difficult or impossible to remove after the healing period without disturbing the position of the implant body 2 and/or damaging the osseointegration between the implant body 2 and the jawbone. On the other hand, if the healing cap 10 is not tightened sufficiently, infection by bacteria or other contaminants may result in the implant body socket or in the gap between the healing cap 10 and the implant body 2. Conventional implant techniques utilize a specially configured torque wrench, such as the wrench disclosed in U.S. Pat. No. 5,734,113 to insure proper torqueing of the healing cap 10. Using such specialized instruments adds to the cost and skill demands of the procedure. In addition, the socket in the implant body 2 may fill with blood or other bodily fluids prior to attaching the healing cap 10 if adequate care is not taken.

The process described above also lacks flexibility. For example, the dental practitioner may wish to use a tool, such as a handpiece or wrench, to transport the implant assembly to the surgical site. The tool can then be used to drive the implant body into the osteotomy. However, the current process typically requires the additional step of removing the implant carrier before attaching the tool to the implant assembly. Furthermore, the dental practitioner typically must either insert the implant assembly into the osteotomy before removing the implant carrier or handle the implant assembly with their hands or an additional tool, which increases the risk of contamination.

Figure 2:
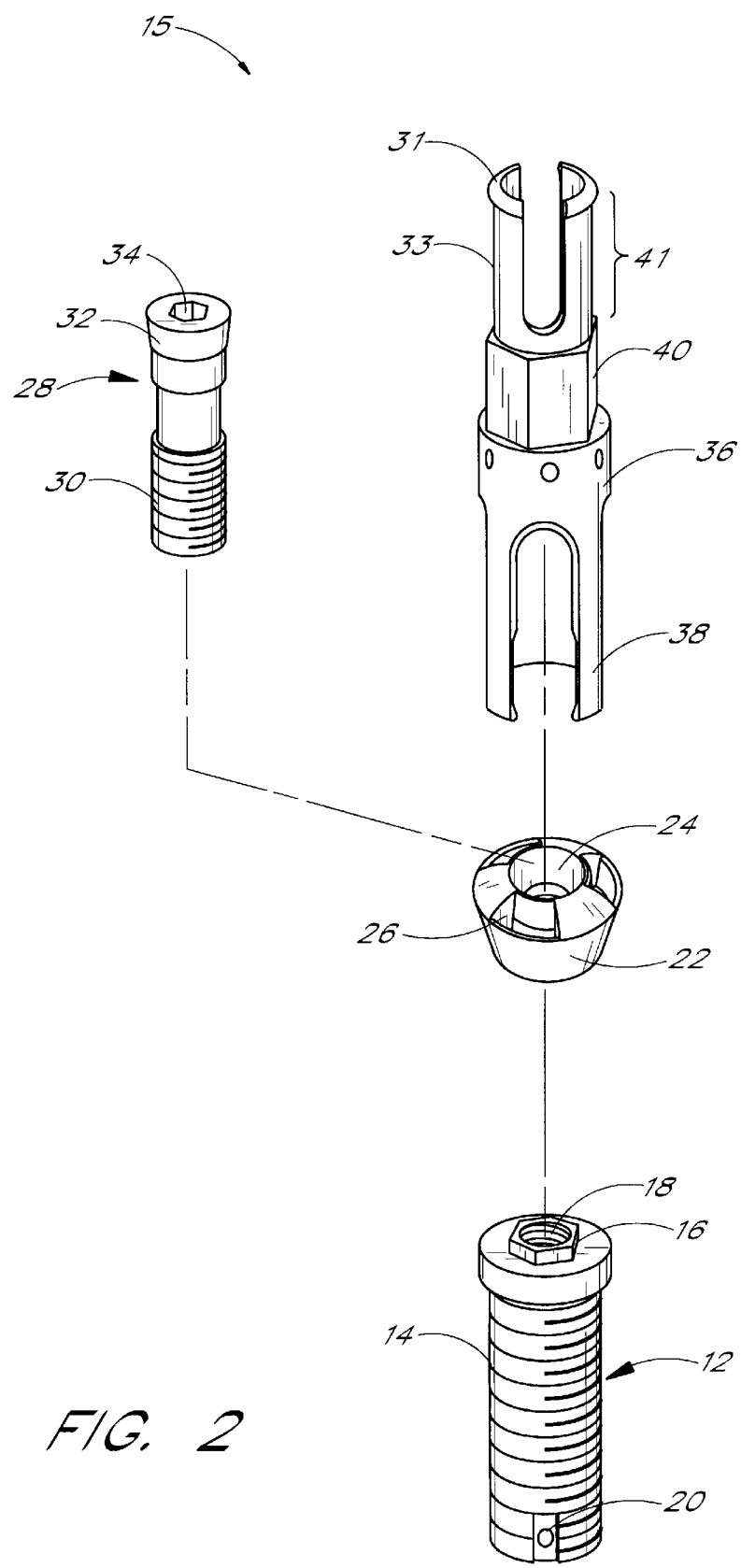
FIG. 2 is an exploded view of one embodiment of a one-step threaded dental implant assembly having features and advantages of the present invention.
Figure 3A:
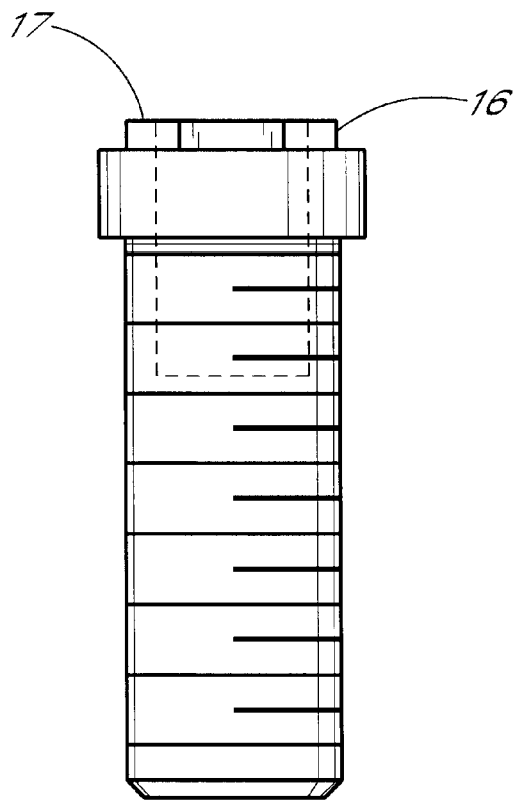
FIG. 3A is a side view of the implant body shown in FIG. 2.
Figure 3B:
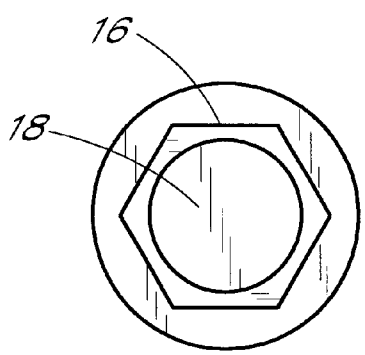
FIG. 3B is a top view of the implant body shown in FIG. 3.

Reference is made in detail to preferred embodiments of the invention, which are illustrated in the accompanying drawings. FIG. 2 shows one embodiment of a one-step threaded implant assembly 15 having features and advantages in accordance with this invention. The implant body 12 is generally cylindrical in shape and has external threads 14 for engagement with the inner wall of an osteotomy formed in a jawbone. As shown in FIGS. 3A and 3B, the implant body 12 includes a threaded socket 18 which is open at the top of implant body 12 and extends longitudinally partway into the implant body. A hexagonal projection 16 is formed at the top of the implant body 12 and is concentrically arranged around the threaded socket 18. The hexagonal projection 16 is integrally attached to and extends away from the implant body 12. The top surface 17 of the hexagonal projection 16 is generally planar and is parallel to the top surface of the implant body 12. The bottom end of the implant body 12 preferably includes a thread-forming portion 20 (see FIG. 2) for allowing self-tapping of the threaded implant. However, it should be appreciated that the threaded implant need not be self-tapping.

Turning to FIGS. 4A, B, C and D, a healing cap 22 is provided for covering the central threaded socket 18 in the implant body 12 during the healing period. The healing cap 22 has a central bore 24 extending through the healing cap 22 along its longitudinal axis. Preferably, the healing cap 22 has a threaded region 23 within a central bore 24. The purpose of the threaded region 23 will be described below. The healing cap 22 also has a female hexagonal recess 25 concentric with the central bore 24 for receiving the hexagonal projection 16 of the implant body 12. With reference to FIGS. 4C and 4D, the healing cap 22 is preferably formed with a plurality of slots 26 located along the perimeter of its top surface which extend partway down into the healing cap 22. The bottom of each slot is formed with an indentation 27.

As shown in FIG. 4A, the healing cap 22 preferably includes a plurality of laser-etched marks 17A, 17B. More preferably, there are four sets of these marks 17A, 17B and each set is equally spaced around the circumference of the healing cap 22 at 90 degree intervals. The top marks 11A are preferably located 1 millimeter from the implant seating surface and are approximately 0.010 inches thick and 0.080 inches wide. The bottom marks 11B are preferably located 0.5 millimeters from the implant seating surface and are approximately 0.005 millimeters thick and 0.040 inches wide. These marks 11A, 11B serve as depth marks that can be used as visual aids to assess implant location in respect to the osteotomy.

Figure 4E:
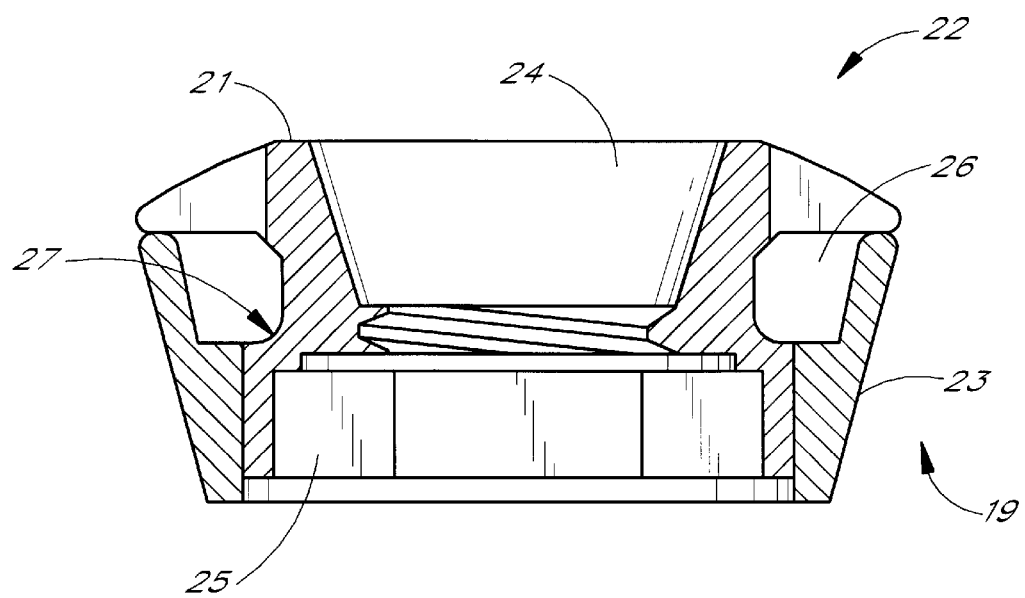
FIG. 4E is a partial cross-sectional view of a healing cap assembly as illustrated in FIG. 2.

The healing cap 22 shown in FIGS. 4A, B, C and D is preferably machined from a single piece of metal. However, as shown in FIG. 4E, the healing cap 22 may be formed from two separate pieces, a collar 21 and a sleeve 19. The collar 21 is preferably press fitted into the sleeve 19. The sleeve 19 and collar are preferably made of dental grade Titanium. However, the outer sleeve may be made of Teflon in order to prevent a shadowing effect. The shadowing effect is caused by contrast of the dark color of a metal component showing through a translucent porcelain crown. Preventing the shadowing effect is especially important with respect to front teeth.

When the healing cap 22 is placed on top of the implant body 12, the female hexagonal recess 25 receives the hexagonal projection 16 such that the healing cap 22 is prevented from rotating relative to the implant body 12. In addition, when the hexagonal projection 16 of the implant body 12 mates with the female recess of the healing cap 22, the socket 18 of the implant body 12 and the bore 24 of the healing cap 22 are collinear. Although a hexagonally shaped protrusion and recess are used in the preferred embodiment, any shape protrusion and corresponding shaped female recess which, when in mating contact, prevents the healing cap from rotating around the male projection may be used to practice the present invention. Accordingly, those skilled in the art will readily appreciate that a wide variety of such mating protrusions, recesses, channels, flats and non-circular cross-sections may be provided, giving due consideration to the aim of providing an interlocking and/or anti-rotational interface between the cap 22 and the implant body 12 to which it is mated.

Similarly, those skilled in the art will readily appreciate that the devices depicted and described herein are not limited to the embodiment whereby the protrusion is provided on the implant body and the mating recess is provided on the healing cap. Alternatively, the protrusion or recess can be provided on either the implant body or the healing cap as desired or expedient, again giving due consideration to the aim of providing an interlocking and/or anti-rotational interface between the cap 22 and the implant body 12 to which it is mated. As an example, the implant body 12 and healing cap 22 may utilize an internal multi-lobed interlocking connection such as the one described in U.S. patent application Ser. No. 09/670,708, filed Sep. 27, 2000, the disclosure of which is incorporated by reference in its entirety herein.

Figure 5:
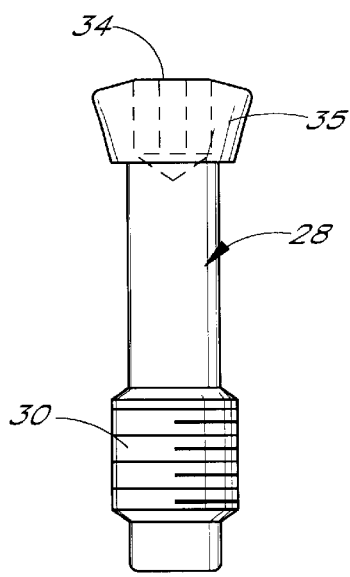
FIG. 5 is a side view of the coupling screw shown in FIG. 2.
Figure 6:
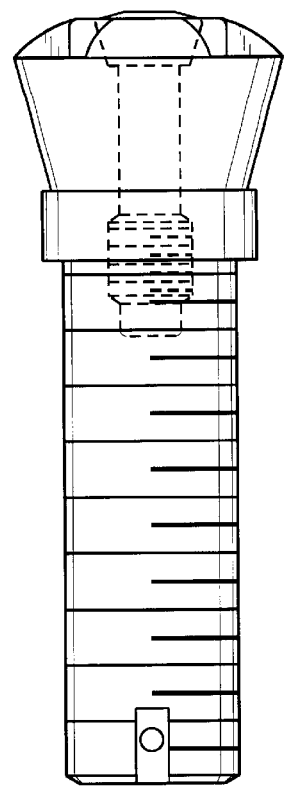
FIG. 6 is a side view of the threaded implant body, healing cap and coupling screw shown in FIG. 2.

Turning now to FIG. 5, a coupling screw 28 is provided for mechanically coupling the healing cap 22 to the implant body 12. The coupling screw 28 extends through the central bore 24 in the healing cap 22 and into the central socket 18 of the implant body 12 (see FIG. 2). The coupling screw 28 has an externally threaded lower portion 30 which passes through the threaded region 23 of central bore 24 and engages the threaded interior of central socket 18 of the implant body 12. The coupling screw 28 has a hexagonal recess 34 located on the top surface. The hexagonal recess 34 allows for the insertion of a hexagonally shaped tool such as a conventional Allen® wrench to remove the healing cap 22 from the implant body 12 after the healing period is complete. As shown in FIG. 6, the coupling screw 28 is pre-installed to mechanically couple the healing cap 22 to the implant body 12 before the implant body 12 and the healing cap 22 are inserted into the jawbone as a single unit. Preferably, the head 35 of the coupling screw 28 is tapered, as illustrated in FIG. 5, in order to allow more of the applied torque to be converted into axial load thereby more securely fastening the healing cap 22 to the implant body 12.

As shown in FIGS. 7A–E, an adapter 36 provides a means for gripping the healing cap 22 during the insertion of the implant body 12 and the healing cap 22 into an osteotomy. The top portion 41 of the adapter 36 includes a plurality (e.g., two or three or four or more) of prongs 33 that are designed to snap fit into either a handpiece driver or an implant carrier as will be described in detail below. Accordingly, each prong preferably includes a protrusion 31 projecting radially outward from the prong 33 for engagement with a similarly formed indentation in the hand piece drive or the implant carrier.

The middle portion of adapter 36 is preferably formed with a hexagonal cross-section 40 to facilitate, if necessary, use of a torque wrench to rotate the adapter 36. The middle portion of the adapter 36 also preferably includes dimples, protrusions 37 or other visual indicia that are aligned with the angled edges of the hexagonal cross-section 40. When the adapter 36 is attached to the healing cap 22 as described below, the edges of the hexagonal cross-section 40 will be aligned with the edges of the hexagonal projection 16 of the implant body 12. Accordingly, the dimples 37 can be used as a visual aid to determine the position of the hexagonal cross-section 40 of the adapter and the position of the hexagonal projection 16 of the implant body 16.

The adapter 36 includes a plurality of prongs 38 which are received into the corresponding slots 26 formed in the top of the healing cap 22 (see FIG. 4C). When the prongs 38 are inserted into slots 26, the adapter 36 is securely coupled to the healing cap 22 and there can be no relative rotation between the adapter 36 and the healing cap 22. The end of each prong 38 preferably includes a lip 39 projecting radially inward for engagement with the similarly formed indentation 27 at the bottom of each slot 26 in the healing cap 22 (see FIGS. 7B, 7C). The slots 26 in healing cap 22 accommodate and engage prongs 38 of the adapter 36 and provide a detent function to prevent inadvertent decoupling of the adapter 36 from the healing cap 22. The lips 39 on the ends of the prongs 38 are preferably tapered or rolled such that the adapter 36 may be removed when desired by applying sufficient pulling force to flex the prongs 38 outward thereby causing the lips 39 to disengage from the indentations 27 in the healing cap 22.

Figure 7A:
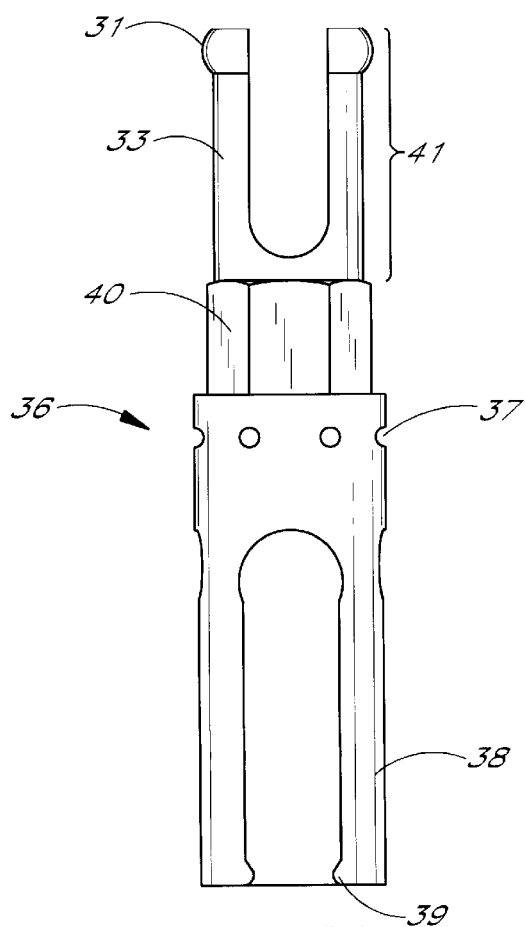
FIG. 7A is a side view of the adapter shown in FIG. 2.
Figures 7B, 7C:
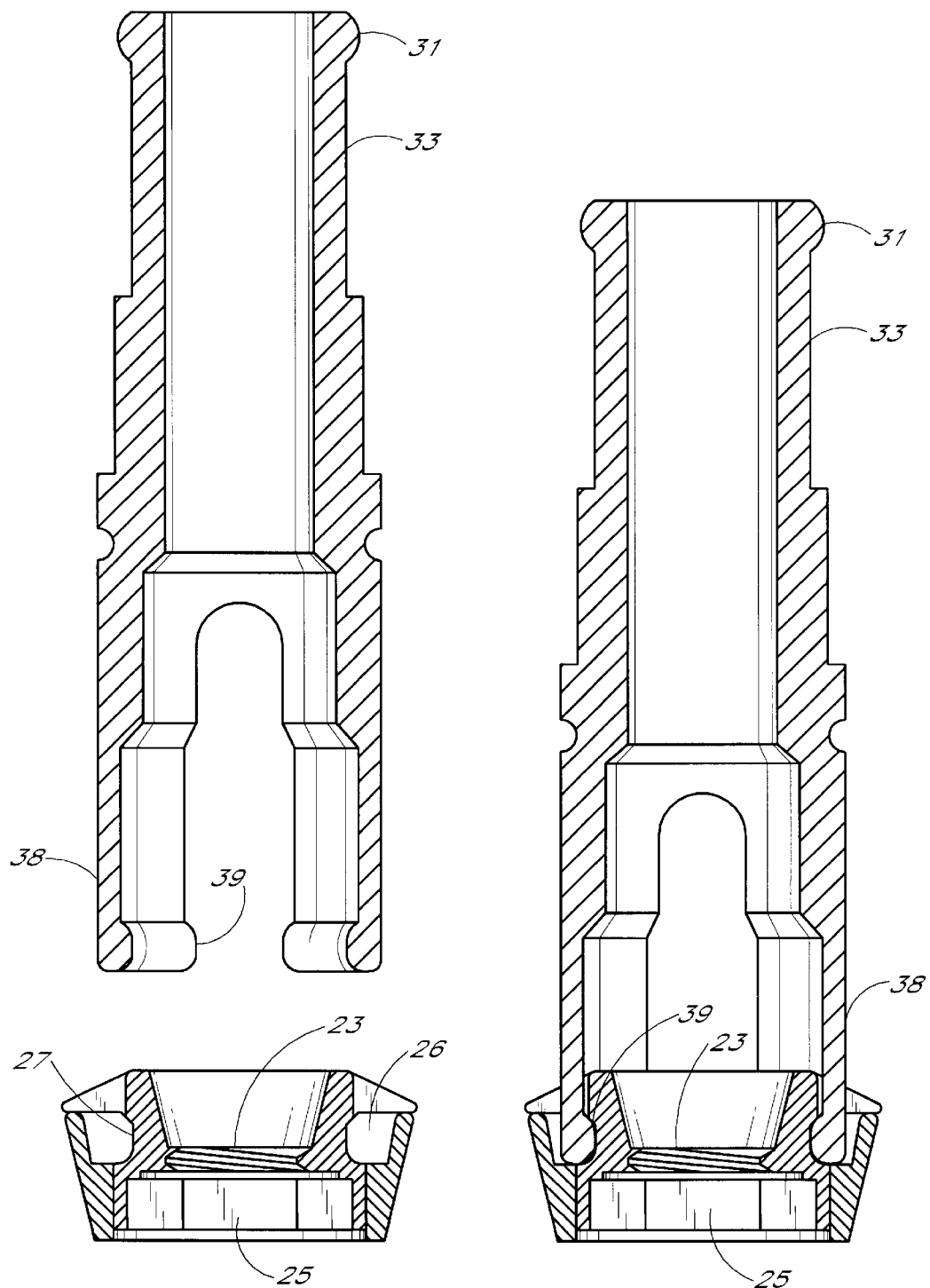
FIG. 7B is a partial cross-sectional view of the adapter of FIG. 7A before insertion into the mating top portion of a healing cap.
FIG. 7C is a partial cross-sectional view of the adapter of FIG. 7A after insertion into the mating top portion of a healing cap.
Figure 7D:
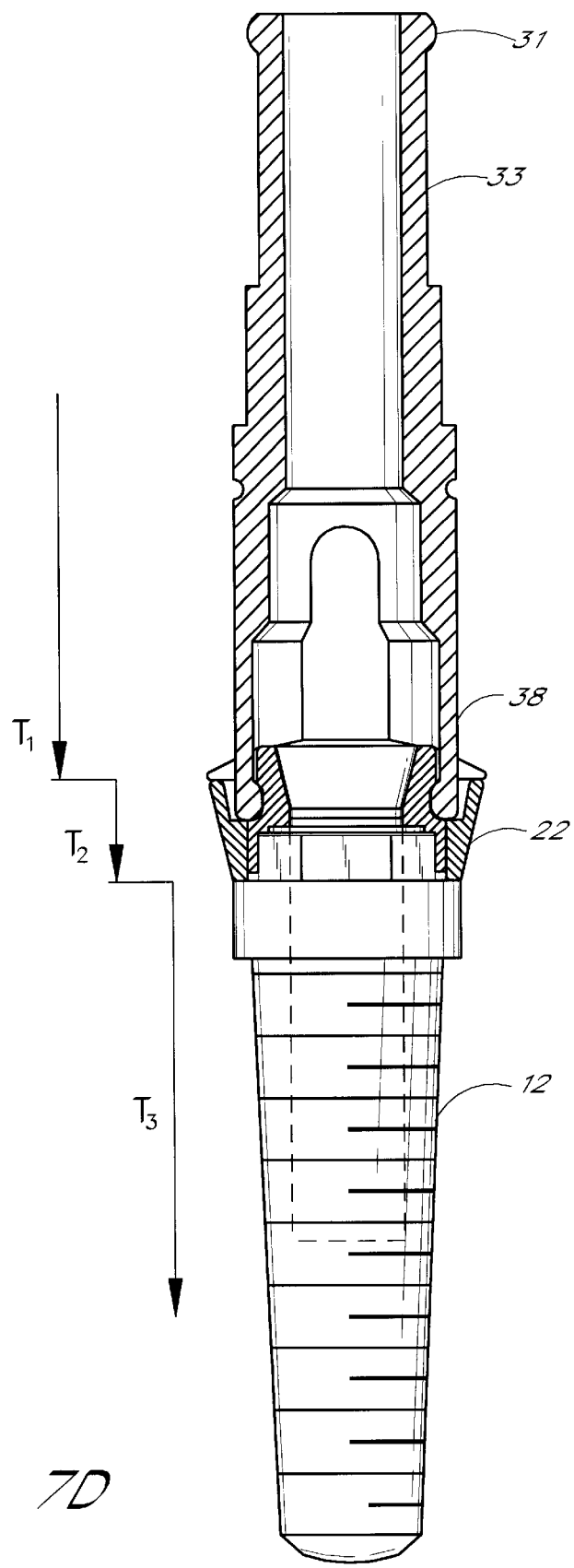
FIG. 7D is a partial cross-sectional view of the adapter of FIG. 7A after insertion into the mating top portion of a healing cap, illustrating the transmission of torque from the adapter to the healing cap and from the healing cap to the implant body.

FIG. 7D is a partial cross-section view of the adapter of FIG. 7A after insertion into the mating top portion of a healing cap, illustrating the transmission of torque from the adapter to the healing cap and from the healing cap to the implant body. In this manner, torque is not transmitted to the coupling screw and, therefore, over-tightening of the healing cap is avoided.

Figure 8A:
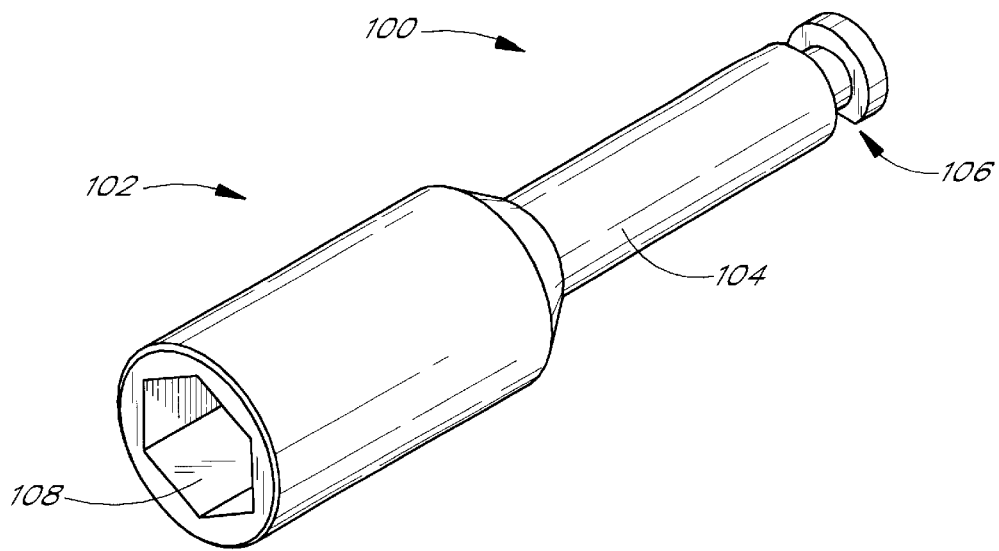
FIG. 8A is a side perspective view of a handpiece driver having features and advantages according to the present invention.
Figure 8B:
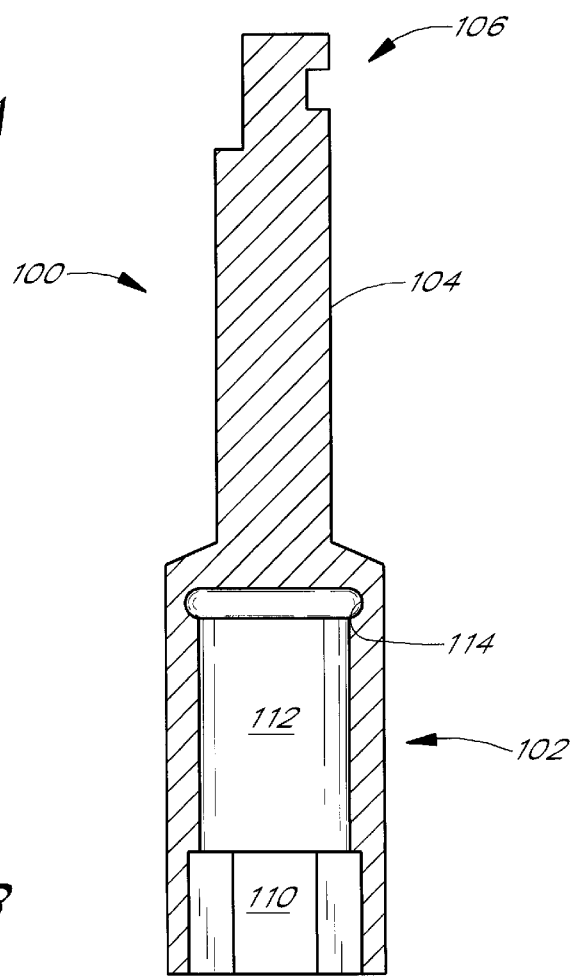
FIG. 8B is side cross-sectional view of the handpiece driver of FIG. 8A.
Figure 8C:
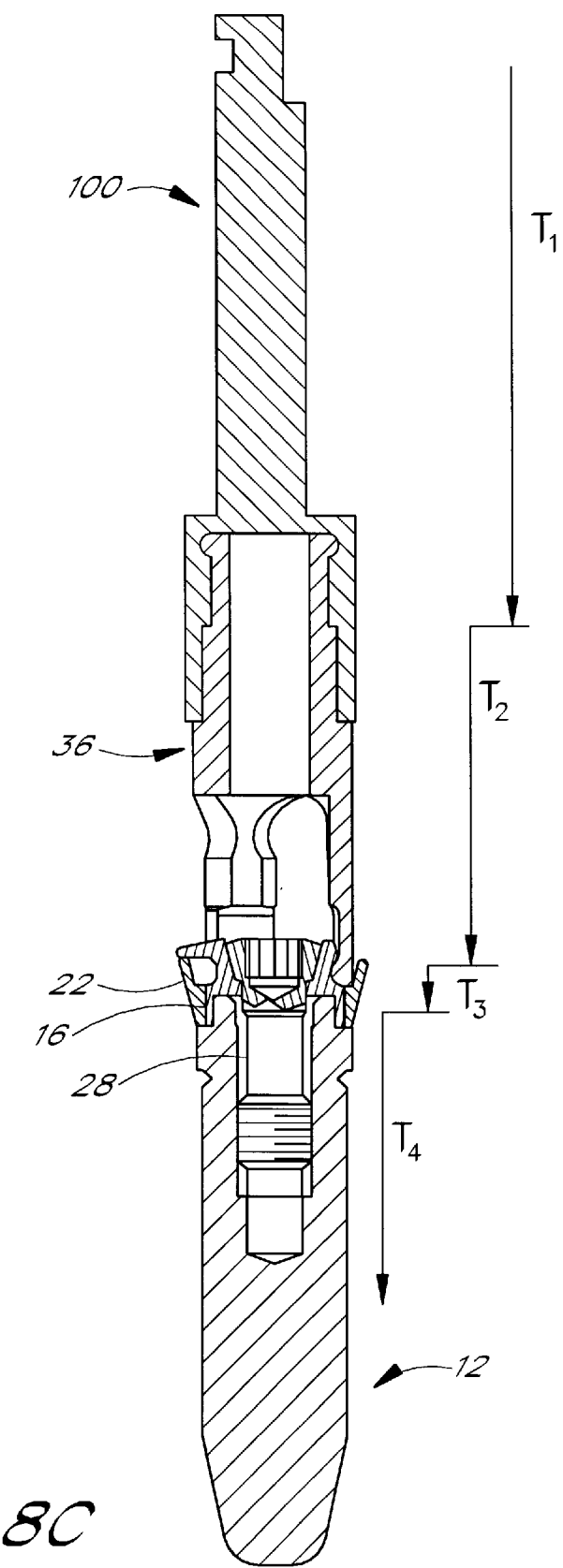
FIG. 8C is a partial cross-sectional view of the handpiece driver of FIG. 8A after insertion into the mating top portion of an adapter, illustrating the transmission of torque from the handpiece driver to the adapter, to the healing cap and from the healing cap to the implant body.

A handpiece driver 100 is illustrated in FIGS. 8A–C. The handpiece driver 100 comprises an adapter receiving portion 102, an elongated portion 104, and a handpiece receiving portion 106. Preferably, all three portions are integrally connected. The adapter receiving portion 102 is formed with an internal passage 108 to receive the top portion of the adapter 36. The internal passage 108 has a hexagonally shaped section 110 for receiving the hexagonal cross-section 40 of adapter 36 and preventing relative rotation between the two.

As shown in FIG. 8B, internal passage 108 also has a prong receiving section 112. The prong receiving section 112 is sized and dimensioned to engage the top portion 41 of the adapter and includes a groove or indentation 114. The prong receiving section 112 accommodates and engages the prongs 33 of the adapter 36 and provides a detent function to prevent inadvertent decoupling of the adapter 36 from the handpiece driver 100. The protrusions 39 of the adapter 36 are preferably tapered or rolled such that adapter 36 may be removed when desired by applying sufficient pulling or rocking force to flex prongs 33 outward thereby causing the protrusions 33 to disengage from the indentations 114 in the handpiece driver 100.

The handpiece receiving portion 106 is sized and dimensioned to fit within the chuck of a commercial dental handpiece drill, which is used to drive the implant body into the osteotomy. Typically, the handpiece portion 106 will include a D-shaped key as depicted in FIGS. 8A and 8B. Accordingly, the handpiece receiving portion 106 is irrotatably locked within the chuck of the dental handpiece so that torque can be transmitted from the handpiece to the handpiece driver 100. The handpiece receiving portion 106 also preferably has a recess that cooperates with a spring loaded plate within the chuck that secures the handpiece portion 106 to the chuck. Although a D-shaped key is used in the preferred embodiment, it should be understood that the key may be in the form other shapes as long as that, when in engaged with the handpiece, the key transmits torque from the handpiece to the handpiece driver 100.

FIG. 8C is a partial cross-section view of the handpiece driver 100 coupled to the dental implant assembly 15 described above. This figure illustrates the transmission of torque T1 from the driver 100 to the adapter 26, torque T2 from the adapter 36 to the healing cap 22, torque T3 from the healing cap 22 to the mating hex 16 of the implant 12 and torque T4 from the mating hex 16 to the implant 12. Advantageously, the torque from the driver 100 is not transferred to the coupling screw 28, which prevents the coupling screw 28 from overtightening.

Figure 9:
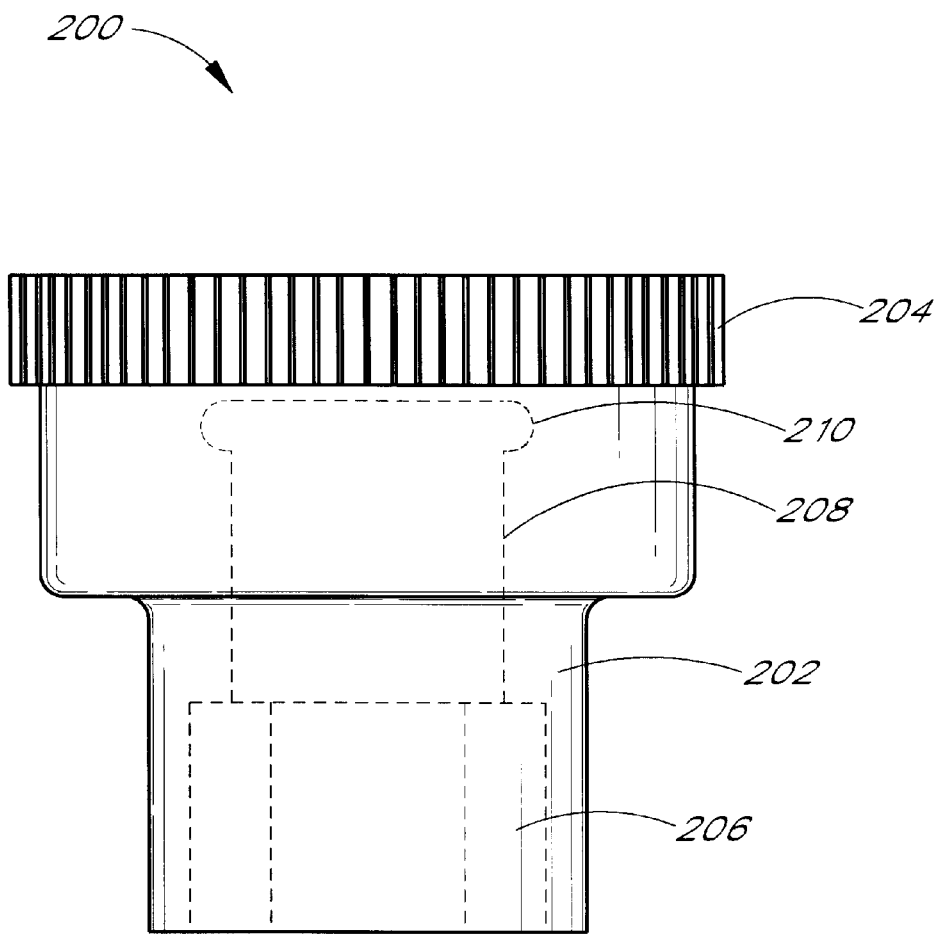
FIG. 9 is a side view of an implant carrier.

FIG. 9 illustrates an implant carrier 200 comprising a body portion 202 and a flange portion 204 preferably integrally connected to the body portion 202. The body portion 202 is formed with an internal passage 206 to receive the top portion of the adapter 36. The internal passage 206 is hexagonally shaped (shown in dotted lines) for receiving the hexagonal cross section 40 of the adapter 36 and preventing relative rotation between the two. An adapter receiving portion 208 is preferably located within the internal passage 206 for gripping the top end 41 of the adapter 36 and securely coupling the implant carrier 200 to the adapter 36. The adapter receiving portion 208 includes at least one indentation 210 configured to engage the protrusions 31 on the top end 41 of the adapter 36. When sufficient longitudinal force is applied to the implant carrier 42, the prongs 33 of the adapter 26 flex and release the adapter 36 from the implant carrier 42.

The flange portion 204 of implant carrier 200 is designed for easy gripping by the practitioner and has a diameter such that sufficient torque can be applied to the implant body 12 by the practitioner to at least initially thread the implant body 12 into an osteotomy formed in the jawbone. Knurling, ridges or other friction enhancing surface structures may be provided. As with the handpiece driver 100, the implant carrier 200 irrotationally mates with the adapter 36, which irrotationally mates with healing cap 22 that, in turn, irrotationally mates with implant body 12. Therefore, all torque applied to the implant carrier 42 by the dental practitioner is transmitted directly to the implant body 12.

Figure 10:
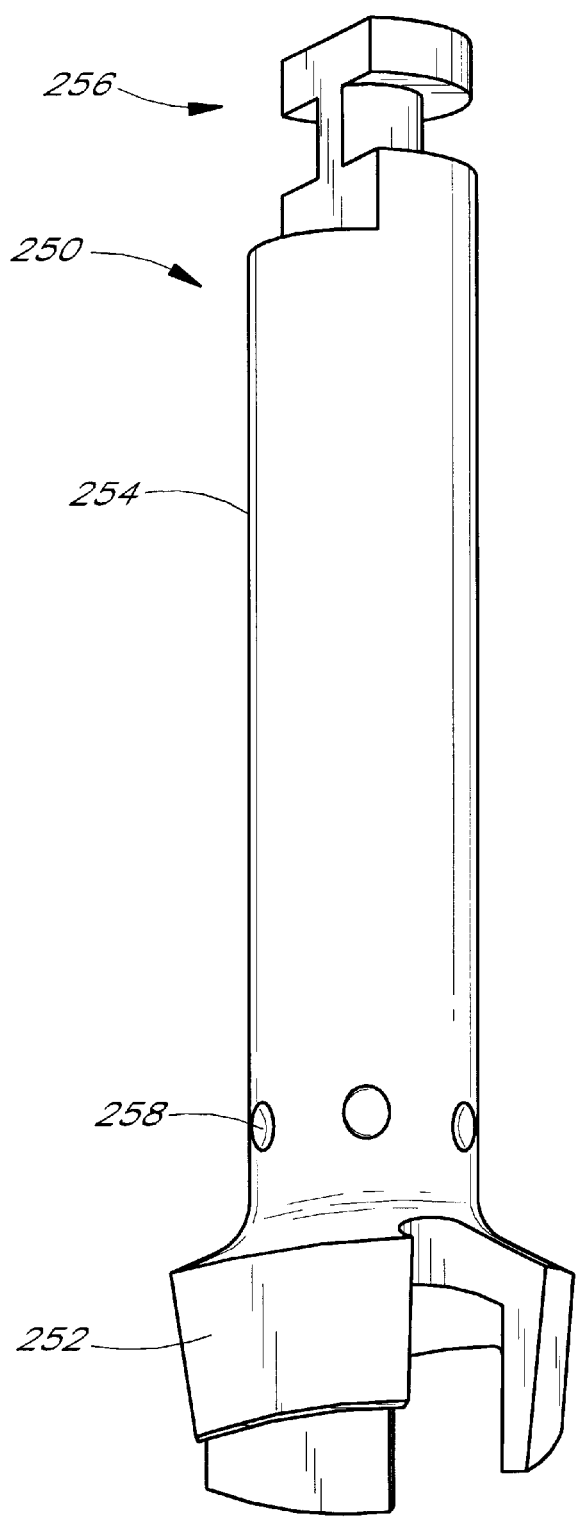
FIG. 10 is a side perspective view of a friction handpiece driver having features and advantages according to the present invention.

FIG. 10 illustrates a friction handpiece adapter 250 comprising a plurality of prongs 252, an elongated section 254, and a handpiece receiving portion 256 similar to the handpiece receiving portion 106 described above. The prongs 252 are configured to fit into the corresponding slots 26 formed on top of the healing cap 22 (see FIG. 4C). However, unlike the prongs of the adaptor 36, the prongs 252 of the illustrated friction handpiece adapter 250 preferably do not include a lip projecting radially inward for engagement with the indentation 27 at the bottom of each slot 26 in the healing cap 22. Accordingly, the friction handpiece adapter 250 does not snap into the healing cap 22 but instead the friction handpiece adapter 250 preferably forms a friction fit with the healing cap 22.

The elongated section 254 preferably includes several dimples 258 or other visual indicia (e.g., protrusions or marks). These dimples 258 are arranges such that, when the friction handpiece adapter 250 is attached to the healing cap 22, the dimples 258 are aligned with the edges of the hexagonal projection 16 of the implant body 11. Accordingly, the dimples 258 can be used as a visual aid to determine the position of the hexagonal projection 16 of the implant body 12.

The implant body 12, healing cap 22, coupling screw 28, and adapter 36 are all preferably made of commercially pure titanium. The implant body 12 may be coated or treated with any number of suitable surface treatments such as acid etching, hydroxylapatite coating and the like to aid in the osseointegration of implant body 12 with the jawbone. Implant carrier 200 is preferably made of a strong and durable plastic. The handpiece driver 200 and the friction handpiece driver 250 are preferably made of titanium or stainless steel.

Figure 11A:
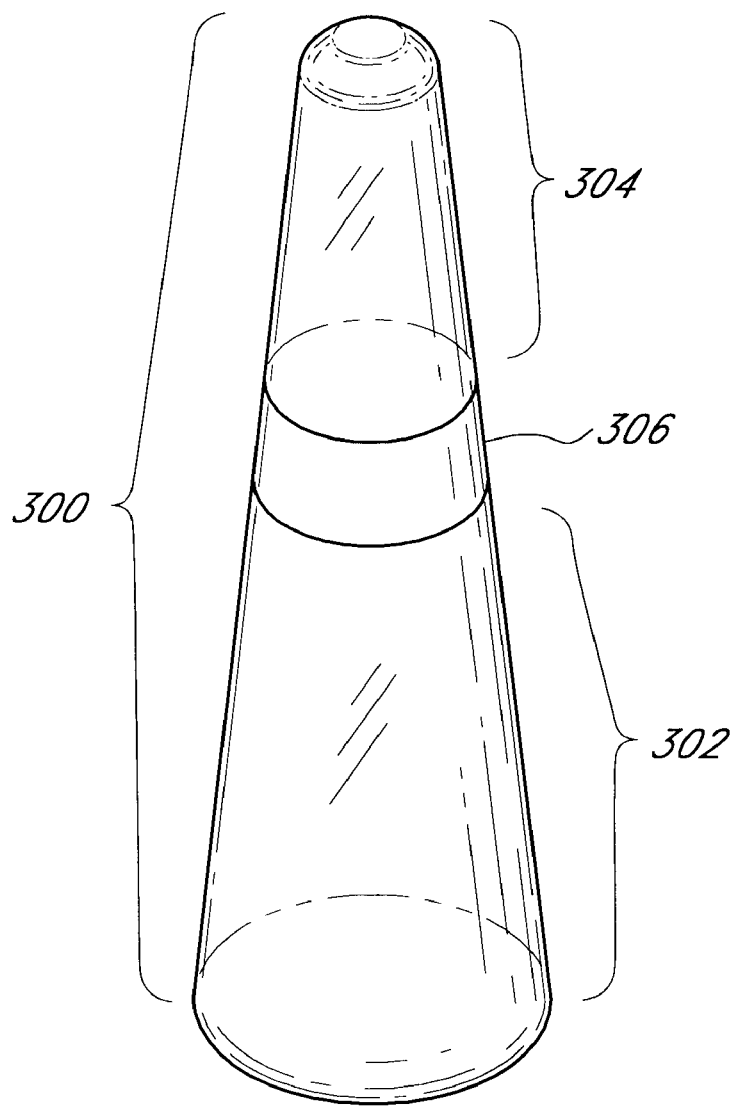
FIG. 11A is a side perspective view of a sterile package for a dental implant assembly having certain features and advantages according to the present invention.
Figure 11B:
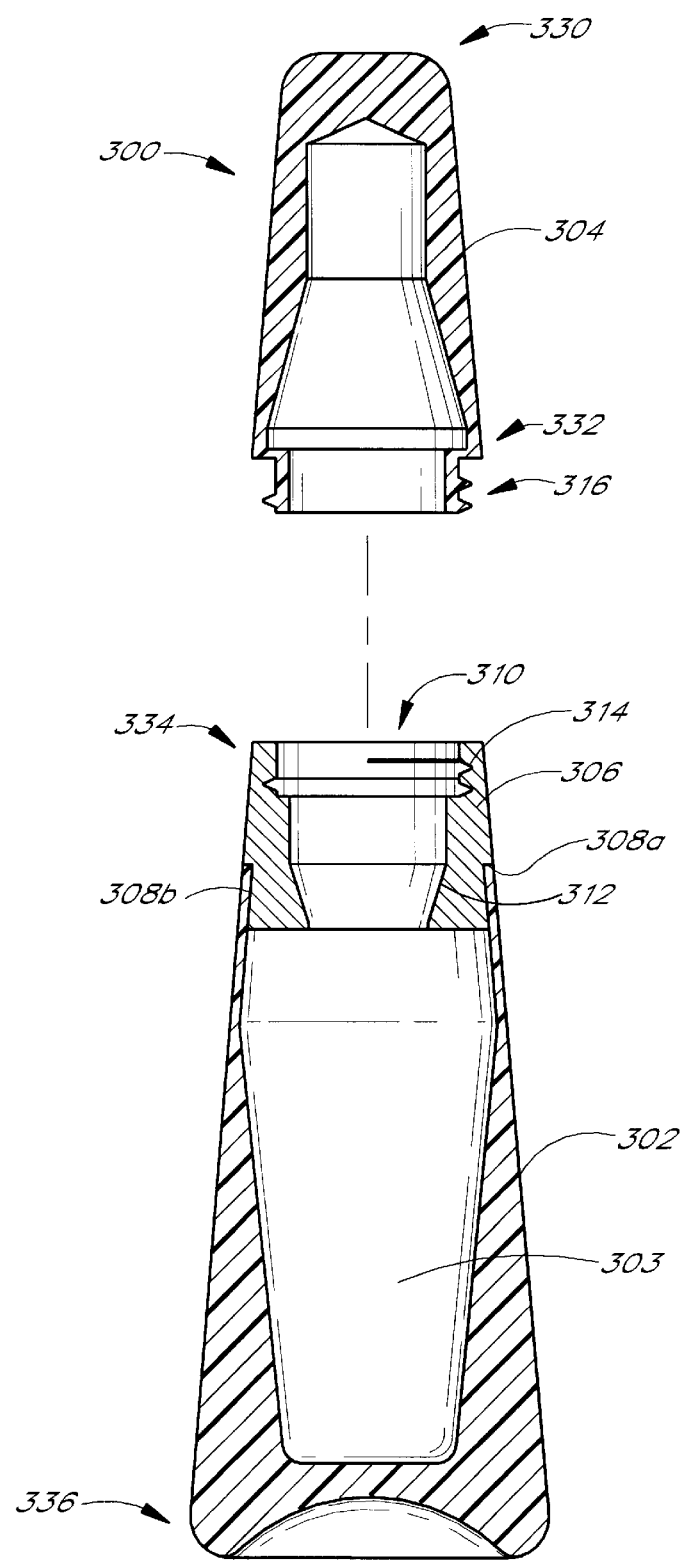
FIG. 11B is an exploded cross-sectional view of the sterile package of FIG. 10A.
Figure 11C:
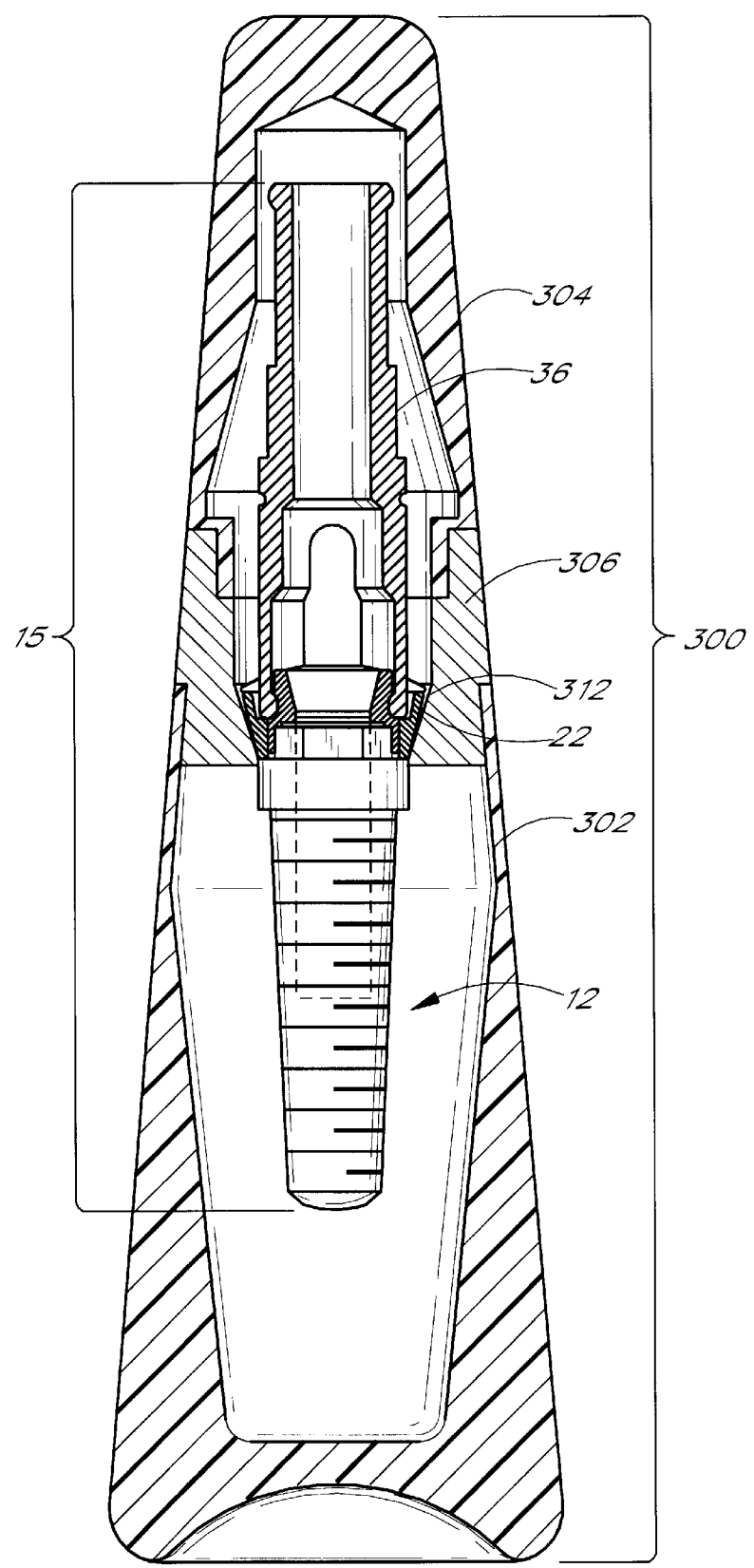
FIG. 11C is a side cross-sectional view of the sterile package of FIG. 10A further including a dental implant assembly.

FIGS. 11A–C illustrate a two-piece sterile package 300 having certain features and advantages according to the present invention. As will be described in detail below, the implant assembly 15, which preferably includes the implant body 12, healing cap 22, coupling screw 28 and adapter 36, is preferably sterilized and packaged in the two-piece sterile package 300.

The sterile package 300 is generally comprised of a bottom piece 302 and a top piece 304. As best seen in FIG. 11B, the bottom piece 302 preferably includes a cavity 303 and a retainer 306, which is suitably supported in the bottom portion 302. In the illustrated arrangement, the retainer 306 is supported by interlocking steps 308a, 308b formed on the retainer 306 and the bottom piece 302. The retainer 306 also includes a central bore 310 that, in the illustrated arrangement, includes a slanted shelf 312 and a threaded portion 314. The slanted shelf 312 is configured to support the implant assembly 15 as shown in FIG. 11C. Advantageously, the shelf 312 supports the implant assembly 15 and prevents it from falling into the bottom of the cavity 303 of the bottom piece 302. The threaded portion 314 is configured to receive a threaded portion 316 of the top piece 304 (see FIG. 11B). As such, the top piece 304 can be threaded into the retainer 306 and on top of the bottom portion 302 so as to seal the implant assembly 15 in the sterile package (see FIG. 11C). The retainer 306 is preferably made of commercially pure titanium. The bottom and top pieces 302, 304 are preferably made of a clear or translucent material, such as polypropylene or polystyrene.

In general, the sterile package 300 thus comprises a first compartment for containing at least a portion of the implant body 12, and a second compartment for containing at least the top portion of the adapter 36. The first and second compartments are preferably each formed at least in part by a rigid wall as has been discussed. The second compartment is openable to expose the adapter 36 for coupling to a tool while the first compartment preferably remains sealed. The first and or second compartments may alternatively be formed or closed by 2 peelable membrane such as a foil or polymeric sheet, blister pack or other openable sterile barrier as will be appreciated by those of skill in the art in view of the disclosure herein. It also should be noted that although disclosed in the context of a threaded implant the sterile packages of the present invention may also be used with implants without threads.

In operation, after a suitable osteotomy has been drilled in the patient's jawbone, the threaded implant body 12 and the healing cap 22 may be inserted pre-assembled into a jawbone in a simple one-step procedure. The dental implant assembly is preferably pre-assembled and provided to the practitioner in the two-piece sterile package, described above, with the healing cap 22 pre-attached to the implant body 12 and the adapter pre-attached to the healing cap 22. As noted above, the healing cap 22 preferably is mechanically coupled to the implant body 12 by the coupling screw 28 which extends through the central bore 24 in the healing cap 22 and into central threaded socket 18 in the implant body 12. Preferably, the coupling screw 28 is pre-installed and is tightened to a predetermined torque setting thereby eliminating the chance of over or under tightening by the practitioner.

Preferably, the dental practitioner holds the lower piece 302 of the two-piece package 300 with one hand and removes the cap 304 with the other hand to expose the top portion 41 of the adapter 36. The practitioner then attaches the handpiece driver 100 to the top portion 41 by pressing the two pieces together. Preferably, the handpiece driver 100 has already been attached to a handpiece. Once the adapter 36 is secured to the handpiece driver 100, the practitioner lifts the implant assembly 15 from the lower piece 302 using the handpiece driver 310 and then positions the implant body 12 over the osteotomy. The practitioner inserts the implant body 12 into the osteotomy by simultaneously pushing down and applying torque to the healing cap 22 via the handpiece. Because healing cap 22 is prevented from rotating relative to implant body 12, the torque applied to healing cap 22 via the handpiece and the adapter 36 is transmitted directly to implant body 12 through the mating hexes described above. Preferably, the handpiece includes means for limiting the amount of torque applied to the implant assembly.

An advantage of the procedure described above is that the practitioner does not touch the implant body 12, the pre-attached healing cap 22 or the adapter 36. Therefore, these components, which have been previously sterilized, remain sterile until they are inserted into the patient's mouth. Accordingly, the present invention reduces the chances for infection, or other complications such as physical damage to the bone ingrowth surface of the implant body 12.

The practitioner screws the implant body 12 to the proper depth, which is indicated by the laser etched marks 11 on the healing cap 22. Once the implant body 12 and the healing cap 22 are satisfactorily seated in the osteotomy, the handpiece driver 310 and the adapter 36 are disengaged from the healing cap 22 by pulling to disengage the prongs 38 from the slots 26 in the healing cap 22. As mentioned above, the lips 39 at the end of prongs 38 on adapter 36 are tapered or rolled to allow for easy removal of the adapter 36 from the healing cap 22. At this point, the implant body 12, healing cap 22 and coupling screw 28 remain in the osteotomy. The gum flap is then placed over the healing cap 22 and the gum tissue is sutured back together thereby covering the implant body 12 and the healing cap 22 and during the initial healing period.

If more delicate control is required, the practitioner may alternatively use the implant carrier 200 (see FIG. 9) instead of the handpiece driver 100 to remove the implant body 12 and the adapter 36 from the sterile package 300 and to insert it into the osteotomy. In this case, once the implant body is positioned over the osteotomy, the practioner inserts the implant body 12 into the osteotomy by simultaneously pushing down and applying torque to the implant carrier 200. Because the healing cap 22 is prevented from rotating relative to the implant body 12, the torque applied to the healing cap 22 via the implant carrier 42 and adapter is transmitted directly to the implant body 12 through the mating hexes described above. If necessary, the implant carrier 200 may be removed from the adapter and a suitable tool such as the handpiece driver 100 or the friction handpiece driver 250 may be inserted into the healing cap 22 and used to complete the threading of the implant into the osteotomy.

In a modified arrangement, the friction handpiece driver 250 (see FIG. 10) can be inserted directly into the healing cap 22 while the implant body 12 remains in the bottom piece 302. Preferably, the friction handpiece driver 250 has already been attached to a handpiece. Once the friction handpiece driver 250 is secured to the healing cap 22, the practitioner lifts the implant assembly 15 from the lower piece 302 using the friction handpiece driver 250 and then positions the implant body 12 over the osteotomy. The practitioner inserts the implant body 12 into the osteotomy by simultaneously pushing down and applying torque to the healing cap 22 via the handpiece. In this modified arrangement, the implant assembly 15 can be packaged within the package 300 without the adapter 36 because the friction handpiece driver 250 is configured to engage the healing cap 22 directly. In yet another modified arrangement, the implant assembly 15 can include the adapter 26, which is preferably removed from the healing cap 22 before the friction handpiece driver 250 is attached to the healing cap 22.

After the initial healing period is complete and the implant body 12 has osseointegrated with the jawbone, an incision is made in the gum tissue to expose and then remove the healing cap 22. A wrench is inserted into the hexagonal recess 34 on the top of the coupling screw 28 and torque is applied to remove the coupling screw 28 from the healing cap 22 and the implant body 12. Due to the threaded region 23 in the healing cap 22 (FIGS. 7C, 7D), the coupling screw 28 remains captured within the healing cap 22 after the coupling screw 28 has been removed from the implant body 12. This feature prevents separation of the coupling screw 28 from the healing cap 22 and reduces the chance of losing a component in the patient's mouth.

Another advantage of the threaded dental implant delivery system described above is its efficiency and ease of use. Because the implant body 12 is inserted into the osteotomy with the healing cap 22 pre-attached, the insertion process is greatly simplified. No insertion post is used in the present invention and therefore there is nothing to disassemble after the implant body is seated in the jawbone. Because there is nothing to disassemble, there is no chance of losing any small components in the patient's mouth. With the present invention, the implant carrier 42 and adapter 36 are detached simply by tugging to disengage the prongs 38 of the adapter 36 from the healing cap 22.

Because the healing cap 22 is pre-attached to the implant body 12, the present invention does not require screwing the healing cap into the implant body after the implant body has been inserted into the jawbone. With existing threaded implant designs, the attachment of the healing cap after the insertion of the implant body into the jawbone is often difficult to accomplish due to the surrounding tissue and blood that can obscure the implant socket from view. Also, it is difficult to ensure sterile conditions inside the implant socket and underneath the healing cap once the implant socket is exposed in the mouth. In contrast, the pre-attached healing cap of the present invention ensures sterile conditions because the implant socket is never exposed during the insertion procedure.

Another advantage of the present design is the increased probability of a successful and stable implantation. With conventional implants, great care must be taken not to under or over tighten the healing cap. An under tightened healing cap may lead to infection and an over tightened healing cap may be difficult to remove without damaging the osseointegration between the implant body and the jawbone. In the present invention, the healing cap is pre-attached to the implant body by the manufacturer with a coupling screw. Because the coupling screw is preset by the manufacturer, there is no chance that the coupling screw will be under or over tightened by the practitioner. This eliminates the possibility of the healing cap being too loose or too tight and therefore reduces the chances of infection or problems removing the healing cap.

Figure 12:
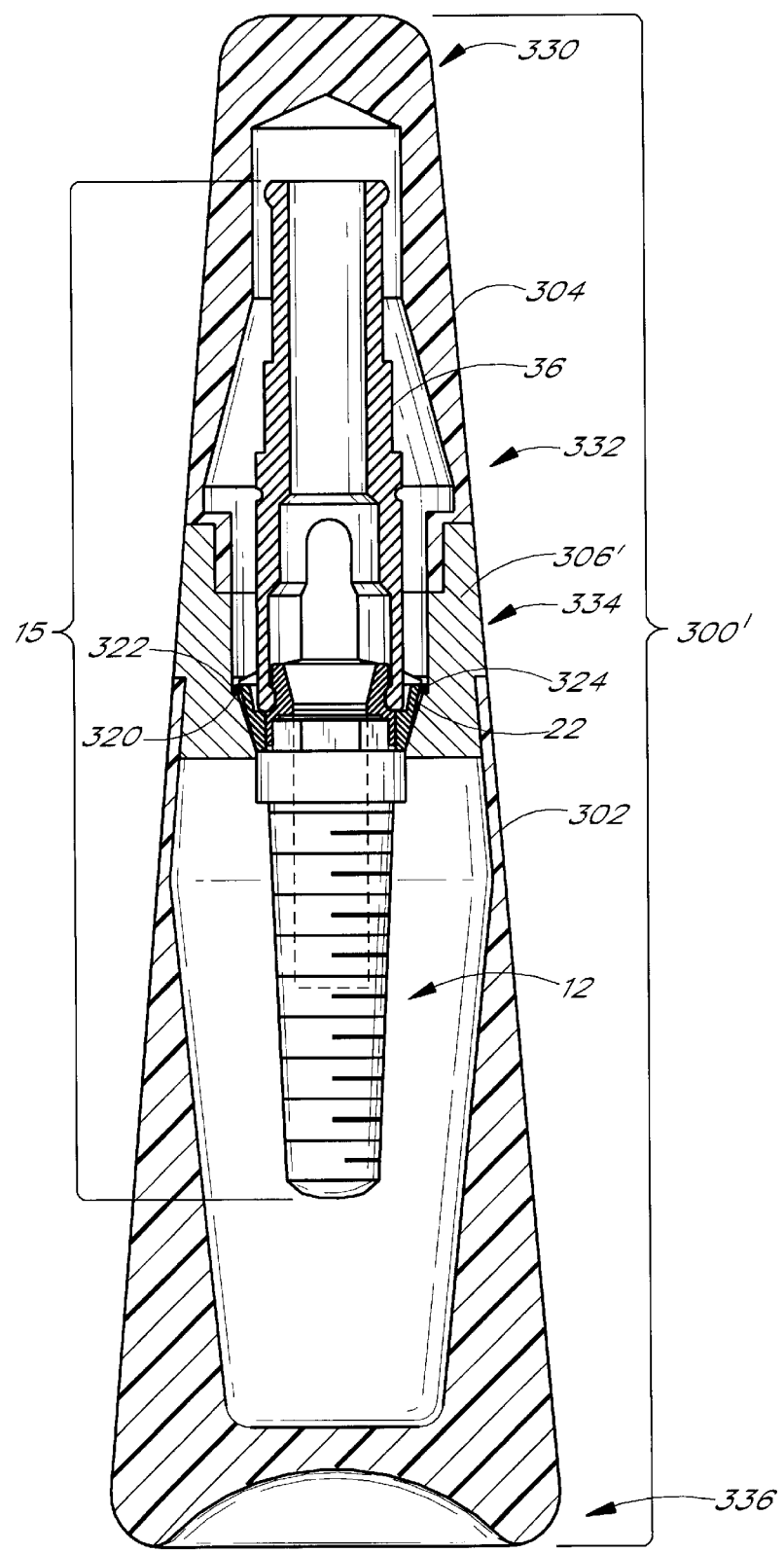
FIG. 12 is a side cross-sectional view of a modified arrangement of a sterile package for a dental implant assembly.

FIG. 12 illustrates a modified arrangement of the sterile package 300' having certain features and advantages according to the present invention. In this arrangement, the retainer 306' is provided with a step 320 formed in the axial wall 322 of the central bore 310. Interlocked in the step 320 is an O-ring 324 or other structure that causes resistant constriction of the size of the bore 310. In this arrangement, the O-ring 320 exerts pressure against the implant assembly 15 so as to prevent the implant assembly 15 from falling out of the package 300 if the top piece 304 is removed and the bottom piece 302 is turned over.

An advantage of the sterile packages 300, 300' illustrated in FIGS. 11B and 12 is that the sterile packages 300, 300' are conical. That is, the top portion 330 of the top piece 304 is preferably narrower than the bottom portion 332 of the top piece 304. In a similar manner, the top portion 334 of the bottom piece 302 is preferably narrower than the bottom portion 336 of the bottom piece 302. This arrangement is preferred because it provides the sterile package 300, 300' with a wider base, which helps to prevent the package 300, 300' from tipping over. The conical shape of the package 300, 300' also helps to prevent the package 300, 300' from rolling off a dental tray or table top if the package 300, 300' is tipped over. Specifically, when tipped over, the package 300, 300' will tend to roll in circles around the more tapered narrower end of the package 300, 300'. As such, the package 300, 300' is less likely to roll off the dental tray or table top.

Figure 13:
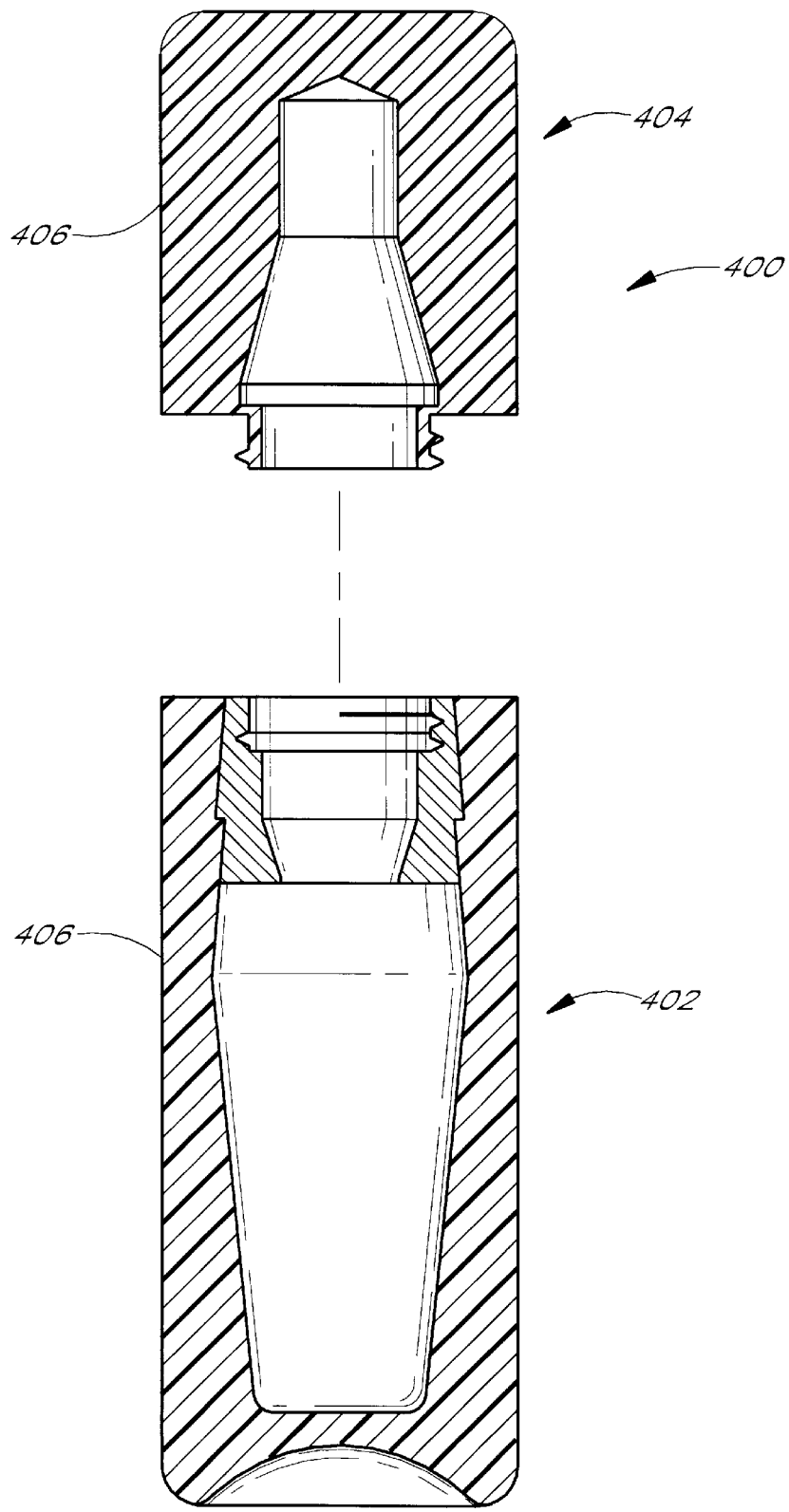
FIG. 13 is a side cross-sectional view of another modified arrangement of a sterile package for a dental implant assembly.

Alternatively, any of a variety of other configurations can be used to minimize or prevent the sterile package from rolling. Generally, one or more flat surfaces may be provided on the exterior surfaces of the sterile package, such as will occur in sterile packages having a polygon (e.g., square, pentagon, hexagon) cross-section. Other roll inhibiting structures may also be used such as one or more axially extending beads or ridges as will be apparent to those of skill in the art. Of course certain features and advantages of the present invention can be achieved in a modified arrangement wherein the package is not conical. For example, FIG. 13 illustrates a modified arrangement of a sterile package 400 having certain features and advantages according to the present invention. In this arrangement, the sterile package 400 is substantially cylindrical in shape. As such, the top piece 402 and the bottom piece 404 have outer walls 406 that are generally parallel to each other.

Figure 14:
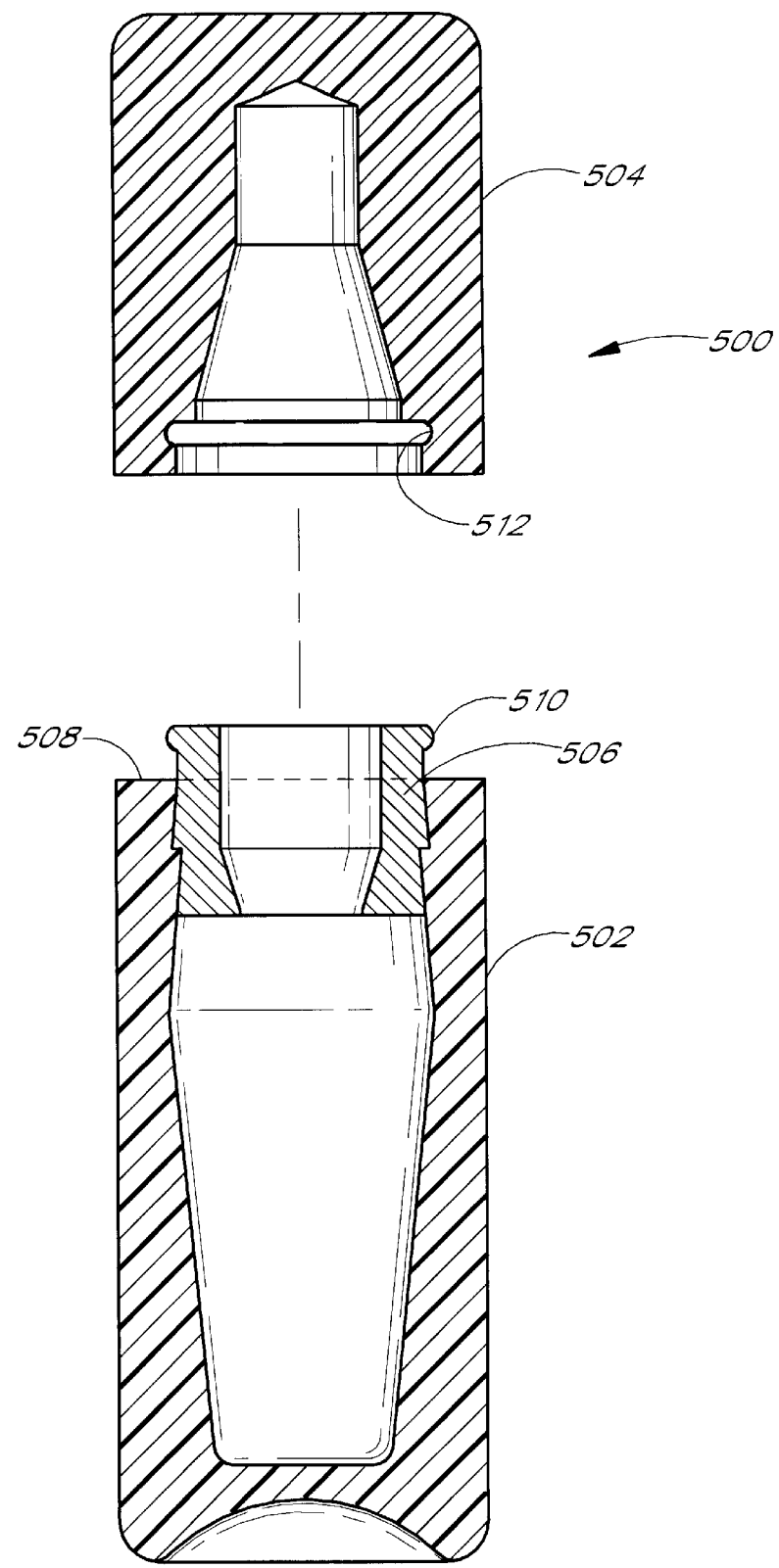
FIG. 14 is a side cross-sectional view of yet another modified arrangement of a sterile package for a dental implant assembly.

FIG. 14 illustrates another modified arrangement of a sterile package 500 having certain features and advantages according to the present invention. This arrangement includes a bottom piece 502 and a top piece 504 as in the previous arrangements. However, in this arrangement, the top piece 504 is configured to snap onto the bottom piece 502. As such, the retainer 506 preferably extends above a top surface 508 of the bottom piece 502. The retainer 506 also includes a protrusion 510 that is configured to fit within a corresponding indentation 512 formed within the top piece 504. Of course, those skilled in the art will recognize that the top and bottom pieces 504, 502 can be modified such that the bottom piece 502 snaps into the top piece 504.

The utility of the present invention will be readily apparent to those skilled in the art. The implant delivery system and method of the present invention provides improved means for inserting a dental implant and healing screw into a patient's jawbone in an efficient one-step process.

Advantageously, the present invention can be adapted for use in conjunction with a wide variety of dental implants. For example, the delivery system described above may also be used with a non-threaded implant. Furthermore, the attachment of the healing cap to the implant body via a small diameter coupling screw, as defined by the present invention, may be performed with or without the one-step features described above. Conventional multi-step implant designs (e.g. wherein an insertion post is used during the insertion procedure) may utilize a healing cap which is attached to the implant body by a coupling screw to protect the implant socket after the implant body is inserted. The coupling screw/healing cap design of the present invention is advantageous to virtually any implant design and may help overcome many of the problems with conventional implants which were discussed above.

It should be noted that certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method for inserting a dental implant comprising the steps of:
    drilling a hole in the jawbone below the gums;
    removing a top portion of a package,
    securing a tool to the implant while the dental implant is supported by a remaining portion of the package, by attaching the tool to an adapter that is pre-attached to a healing cap, which is pre-attached to the dental implant;
    removing the dental implant from the remaining portion of the package;
    transporting the dental implant to the hole in the jawbone;
    applying torque to the dental implant via the tool; and
    disengaging the tool from the dental implant.

2. The method of claim 1, wherein the removing a top portion step includes unscrewing the top portion from the remaining portion.

3. The method of claim 1, wherein the removing a top portion step includes unsnapping the top portion from the remaining portion.

4. The method of claim 1, wherein the removing a top portion step of the package includes exposing a top portion of the adapter that is pre-attached to the healing cap.

5. The method of claim 4, wherein the disengaging the tool from the dental implant steps includes disengaging the adapter from the healing cap.

6. The method of claim 1, wherein the removing a top portion step of the package step includes exposing a top portion of the adapter.

7. The method of claim 6, wherein the disengaging the tool from the dental implant step includes disengaging the adapter from the healing cap, which is attached to the dental implant.

8. The method of claim 1, wherein the securing the tool to the dental implant step includes holding the remaining portion of the package in one hand while holding the tool in another hand.

9. The method of claim 1, wherein the tool is a dental handpiece.

10. The method of claim 1, wherein the tool is an implant carrier.

11. The method of claim 1, wherein the tool is a friction handpiece driver.

12. A package for storing a dental implant assembly in a sterile environment comprising a first portion and a second portion that is attached to the first portion, the dental implant assembly including at least a dental implant, a healing cap that is pre-attached to the dental implant and an adapter that is secured to the dental implant via the healing cap, the package being configured such that when the first portion is separated from the second portion an upper portion of the adapter is exposed while the dental implant remains contained within the second portion.

13. The package according to claim 12, wherein the package is conically shaped.

14. A dental implant delivery system to be used in implanting a dental implant within an osteotomy formed in a jawbone, comprising:
    a dental implant having a top end and a bottom end, the bottom end being insertable into the osteotomy, the dental implant further having a threaded central socket extending from the top end toward the bottom end, the socket being open at the top end of the dental implant;
    a healing cap having a top and a bottom and a central bore extending therethrough, the healing cap sized and shaped so as to sealingly engage the top end of the dental implant to substantially prevent bacteria or debris from entering the central socket during an initial healing period, the healing cap further comprising a first connector for receiving a torque drive adapter;
    the torque drive adapter having a top end and a bottom end, the bottom end of the adapter being formed with a second connector which is engageable with the first connector in the top of the cap for engaging and applying torque to the cap to thread the dental implant into the hole formed in the jaw bone;
    the top end of the dental implant and/or the bottom of the healing cap further having a rotational lock to prevent relative rotation of the healing cap and the dental implant when the healing cap is engaged with the dental implant;
    a coupling screw having a head seated against the top of the healing cap and a shaft extending through the central bore in the healing cap and threading into the threaded socket in the dental implant, the coupling screw securely coupling the healing cap to the implant body; and
    a package that includes a top piece and a bottom piece;
    wherein the dental implant, the healing cap, the coupling screw, and the torque driver adapter are pre-assembled and packaged and supported in the package such that when the top piece is removed the top end of the torque driver adapter is exposed.

15. The dental implant delivering system as in claim 14, wherein the sterile package is cylindrically shaped.

16. The dental implant delivering system as in claim 14, wherein the sterile package is conically shaped.

17. A dental implant delivery system to be used in implanting a dental implant within an osteotomy formed in a jawbone, comprising:

a dental implant having a top end and a bottom end, the bottom end being insertable into the osteotomy, the dental implant further having a threaded central socket extending from the top end toward the bottom end, the socket being open at the top end of the dental implant;

a healing cap having a top and a bottom and a central bore extending therethrough, the healing cap sized and shaped so as to sealingly engage the top end of the dental implant to substantially prevent bacteria or debris from entering the central socket during an initial healing period, the healing cap further comprising a first connector for receiving a torque drive adapter;

the torque drive adapter having a top end and a bottom end, the bottom end of the adapter being formed with a second connector which is engageable with the first connector in the top of the cap for engaging and applying torque to the cap to thread the dental implant into the hole formed in the jaw bone;

the top end of the dental implant and/or the bottom of the healing cap further having a rotational lock to prevent relative rotation of the healing cap and the dental implant when the healing cap is engaged with the dental implant;

a coupling screw having a head seated against the top of the healing cap and a shaft extending through the central bore in the healing cap and threading into the threaded socket in the dental implant, the coupling screw securely coupling the healing cap to the implant body; and a package that includes a top piece and a bottom piece;

wherein the dental implant, the healing cap, the coupling screw, and the torque driver adapter are pre-assembled and packaged and supported in the package such that when the top piece is removed the top end of the torque driver adapter is exposed and wherein the bottom portion of the sterile package includes a retainer that has a bore with a tapered section configured to support the healing cap.

18. The dental implant delivery system as in claim 17, wherein the retainer further includes an O-ring that is configured to secure the dental implant within the bottom portion of the two-piece package.

19. The dental implant delivering system as in claim 18, wherein the sterile package is cylindrically shaped.

20. The dental implant delivering system as in claim 18, wherein the sterile package is conically shaped.

21. The dental implant delivery system as in claim 17, wherein the first connector comprises a plurality of slots formed along the periphery of the top of the healing cap and the second connector comprises a plurality of prongs insertable into the slots.

22. The dental implant delivering system as in claim 21, wherein the sterile package is cylindrically shaped.

23. The dental implant delivering system as in claim 21, wherein the sterile package is conically shaped.

24. The dental implant delivering system as in claim 17, wherein the sterile package is cylindrically shaped.

25. The dental implant delivering system as in claim 17, wherein the sterile package is conically shaped.

* * * * *